(12) United States Patent
Shetty et al.

(10) Patent No.: US 10,342,966 B2
(45) Date of Patent: *Jul. 9, 2019

(54) DEVICES FOR TARGETED DELIVERY OF THERAPEUTIC IMPLANTS

(71) Applicant: UNL Holdings LLC, New York, NY (US)

(72) Inventors: Gautam N. Shetty, Pikesville, MD (US); Aaron M. Weir, York Haven, PA (US); Christian P. Brandt, York, PA (US); Lou Castagna, Middletown, PA (US); Tod H. Brenner, Pequea, PA (US)

(73) Assignee: UNL Holdings LLC, New York, NY (US)

( * ) Notice: Subject to any disclaimer, the term of this patent is extended or adjusted under 35 U.S.C. 154(b) by 790 days.

This patent is subject to a terminal disclaimer.

(21) Appl. No.: 14/708,778

(22) Filed: May 11, 2015

(65) Prior Publication Data

US 2015/0238745 A1 Aug. 27, 2015

Related U.S. Application Data

(62) Division of application No. 13/775,155, filed on Feb. 23, 2013, now Pat. No. 9,050,415.

(Continued)

(51) Int. Cl.
*A61M 37/00* (2006.01)
*A61M 5/32* (2006.01)
*A61M 5/31* (2006.01)

(52) U.S. Cl.
CPC .......... *A61M 37/0069* (2013.01); *A61M 5/32* (2013.01); *A61M 5/3232* (2013.01);
(Continued)

(58) Field of Classification Search
CPC ................ A61M 5/3234; A61M 5/508; A61M 37/0069; A61M 5/3232; A61M 5/502;
(Continued)

(56) References Cited

U.S. PATENT DOCUMENTS

| 4,838,863 A | 6/1989 | Allard et al. |
| 4,838,869 A | 6/1989 | Allard et al. |

(Continued)

FOREIGN PATENT DOCUMENTS

| DE | 19740259 A | 3/1998 |
| EP | 1 300 173 B1 | 6/2006 |

(Continued)

OTHER PUBLICATIONS

European Patent Office, International Search Report in International Application No. PCT/US2012/067793, 5 pages (May 31, 2013).

(Continued)

*Primary Examiner* — Kami A Bosworth
*Assistant Examiner* — Alexandra Lalonde
(74) *Attorney, Agent, or Firm* — Hamilton, Brook, Smith & Reynolds, P.C.

(57) ABSTRACT

A barrel adapter mountable to a syringe barrel includes a barrel tip, a needle assembly, a stylet assembly slidably disposed within a needle lumen of the needle assembly, and a plug within the lumen of the needle. An implant delivery syringe includes a barrel, a plunger assembly, and the barrel adapter. The syringe may include a needle retraction mechanism having a biasing member and an actuable locking arrangement. When the actuable locking arrangement is actuated, the biasing member causes the needle to axially translate over the stylet during retraction to dislodge the plug and cause delivery of an implant to a target location. The plug may be a biodegradable polymer plug such as a water-soluble polymer, PLGA, and/or CARP. The stylet may (Continued)

be retracted following delivery. Methods of assembling implant delivery syringes with drug implants are also provided.

5 Claims, 10 Drawing Sheets

Related U.S. Application Data

(60) Provisional application No. 61/602,277, filed on Feb. 23, 2012, provisional application No. 61/639,898, filed on Apr. 28, 2012, provisional application No. 61/667,010, filed on Jul. 2, 2012, provisional application No. 61/677,186, filed on Jul. 30, 2012, provisional application No. 61/767,369, filed on Feb. 21, 2013.

(52) U.S. Cl.
CPC ... *A61M 5/3234* (2013.01); *A61M 2005/3131* (2013.01); *A61M 2005/323* (2013.01); *A61M 2005/3236* (2013.01); *F04C 2270/041* (2013.01); *Y10T 29/49826* (2015.01)

(58) Field of Classification Search
CPC .... A61M 5/322; A61M 5/158; A61M 5/3221; A61M 2005/5033; A61M 2005/5046; A61M 2005/3231; A61M 2005/323; A61M 2005/3223; A61M 2005/3224; A61M 2005/3235; A61M 2005/3236; A61M 2005/3238; A61M 2005/3239; A61M 2005/3241; A61M 2005/3131; A61M 31/007; A61F 9/0017; A61F 9/0026; A61F 9/0008; A61F 2/167; A61B 17/3468; A61B 2090/3987; A61D 7/00
See application file for complete search history.

(56) References Cited

U.S. PATENT DOCUMENTS

| | | | |
|---|---|---|---|
| 4,874,382 | A | 10/1989 | Lindemann et al. |
| 4,927,414 | A | 5/1990 | Kulli |
| 4,994,034 | A | 2/1991 | Botich et al. |
| 5,053,010 | A | 10/1991 | McGary et al. |
| 5,114,410 | A | 5/1992 | Caralt Batlle |
| 5,180,369 | A | 1/1993 | Dysarz |
| 5,180,370 | A | 1/1993 | Gillespie |
| 5,188,599 | A | 2/1993 | Botich et al. |
| 5,211,629 | A | 5/1993 | Pressly et al. |
| 5,304,138 | A | 4/1994 | Mercado |
| 5,342,310 | A | 8/1994 | Ueyama et al. |
| 5,346,480 | A | 9/1994 | Hess et al. |
| 5,385,551 | A | 1/1995 | Shaw |
| 5,389,076 | A | 2/1995 | Shaw |
| 5,466,233 | A | 11/1995 | Weiner et al. |
| 5,578,011 | A | 11/1996 | Shaw |
| 5,613,952 | A | 3/1997 | Pressly, Sr. et al. |
| 5,769,822 | A | 6/1998 | McGary et al. |
| 5,800,403 | A | 9/1998 | Pressly, Sr. et al. |
| 5,941,250 | A | 8/1999 | Aramant et al. |
| 6,015,438 | A | 1/2000 | Shaw |
| 6,074,370 | A | 6/2000 | Pressly, Sr. et al. |
| 6,123,683 | A | 9/2000 | Propp |
| 6,159,218 | A | 12/2000 | Aramant et al. |
| 6,190,350 | B1 | 2/2001 | Davis et al. |
| 6,447,522 | B2 | 9/2002 | Gambale et al. |
| 6,450,937 | B1* | 9/2002 | Mercereau ........ A61M 37/0069 600/7 |
| 6,478,768 | B1 | 11/2002 | Kneer |
| 6,478,776 | B1 | 11/2002 | Rosenman et al. |
| 6,494,863 | B1 | 12/2002 | Shaw et al. |
| 6,558,357 | B1 | 5/2003 | Hoeck |
| 6,605,073 | B1 | 8/2003 | Pressly, Sr. et al. |
| 6,632,171 | B2 | 10/2003 | Iddan et al. |
| 6,673,044 | B2 | 1/2004 | Righi et al. |
| 6,752,782 | B2 | 6/2004 | Liao |
| 6,899,717 | B2 | 5/2005 | Weber et al. |
| 7,014,622 | B1 | 3/2006 | Pressly, Sr. et al. |
| 7,090,681 | B2 | 8/2006 | Weber et al. |
| 7,147,644 | B2 | 12/2006 | Weber et al. |
| 7,329,238 | B2 | 2/2008 | Halseth et al. |
| 7,468,065 | B2 | 12/2008 | Weber et al. |
| 7,572,247 | B2 | 8/2009 | Smith et al. |
| 7,604,613 | B2 | 10/2009 | Crawford et al. |
| 7,713,244 | B1 | 5/2010 | Cherif Cheikh et al. |
| 7,753,916 | B2 | 7/2010 | Weber et al. |
| 7,806,858 | B2 | 10/2010 | Smith et al. |
| 7,947,020 | B2 | 5/2011 | Thayer |
| 7,972,300 | B2 | 7/2011 | Smith et al. |
| 7,972,301 | B2 | 7/2011 | Oliver |
| 7,976,489 | B2 | 7/2011 | Lawter et al. |
| 7,988,663 | B2 | 8/2011 | Schiller et al. |
| 7,993,307 | B2 | 8/2011 | Lin |
| 7,998,108 | B2 | 8/2011 | Nazzaro et al. |
| 8,029,458 | B2* | 10/2011 | Cherif-Cheikh ............. A61M 37/0069 604/197 |
| 8,088,104 | B2 | 1/2012 | Smith et al. |
| 8,152,762 | B2 | 4/2012 | Smith et al. |
| 8,192,408 | B2 | 6/2012 | Nazzaro et al. |
| 8,242,099 | B2 | 8/2012 | Wong et al. |
| 8,343,094 | B2 | 1/2013 | Shaw |
| 8,702,653 | B2 | 4/2014 | Samandi et al. |
| 8,979,795 | B2* | 3/2015 | Bokelman ........... A61M 5/3221 604/110 |
| 9,050,415 | B2 | 6/2015 | Shetty et al. |
| 2003/0233101 | A1* | 12/2003 | Lubock ............. A61M 37/0069 606/116 |
| 2006/0084943 | A1 | 4/2006 | Rosenman et al. |
| 2007/0178138 | A1* | 8/2007 | Pal ........ A61K 9/0024 424/426 |
| 2008/0097337 | A1 | 4/2008 | Judd et al. |
| 2009/0118703 | A1 | 5/2009 | Orilla et al. |
| 2009/0209903 | A1 | 8/2009 | Cherif-Cheikh et al. |
| 2009/0258924 | A1 | 10/2009 | Lyons et al. |
| 2011/0040245 | A1 | 2/2011 | Garcia De Castro Andrews |
| 2011/0152755 | A1 | 6/2011 | Schmalz |
| 2011/0190699 | A1 | 8/2011 | Judd et al. |
| 2011/0230844 | A1 | 9/2011 | Shaw et al. |
| 2011/0275891 | A1 | 11/2011 | Shemi |
| 2012/0123324 | A1* | 5/2012 | Schmalz ........... A61B 17/3468 604/63 |
| 2013/0226084 | A1 | 8/2013 | Samandi et al. |
| 2013/0237910 | A1 | 9/2013 | Shetty et al. |
| 2014/0213972 | A1 | 7/2014 | Samandi et al. |
| 2014/0276446 | A1 | 9/2014 | Bokelman et al. |
| 2015/0202419 | A1 | 7/2015 | Wetzel et al. |

FOREIGN PATENT DOCUMENTS

| | | |
|---|---|---|
| EP | 2011530 A1 | 1/2009 |
| EP | 1 633 433 B1 | 4/2010 |
| EP | 2229969 A | 9/2010 |
| JP | 2011-125724 A | 6/2011 |
| WO | WO 2005-072802 A1 | 8/2005 |
| WO | WO 2006-024172 A | 3/2006 |
| WO | WO 2012/027182 A1 | 3/2012 |
| WO | WO 2013/126853 A2 | 8/2013 |
| WO | WO 2016/160004 | 10/2016 |

OTHER PUBLICATIONS

European Patent Office, Written Opinion of the International Searching Authority in International Application No. PCT/US2012/067793, 5 pages (May 31, 2013).

European Patent Office, International Search Report in International Patent Application No. PCT/US2013/027529, 5 pages (Sep. 2, 2013).

(56) References Cited

OTHER PUBLICATIONS

European Patent Office, Written Opinion of the International Searching Authority in International Patent Application No. PCT/US2013/027529, 6 pages (Sep. 2, 2013).
International Preliminary Report on Patentability for Int'l Application No. PCT/US2013/027529, titled: Devices for Targeted Delivery of Therapeutic Implants, dated Aug. 26, 2014.
International Preliminary Report on Patentability in International Application No. PCT/US2012/067793, titled: Retractable Needle Safety Syringes, 5 pages, Completed: Jul. 29, 2014.
International Search Report for Int'l Application No. PCT/US2015/023789, titled: Devices for Targeted Delivery of Therapeutic Implants dated Feb. 3, 2016.
Written Opinion for Int'l Application No. PCT/US2015/023789, titled: Devices for Targeted Delivery of Therapeutic Implants, dated Feb. 3, 2016.
International Preliminary Report on Patentability for Int' Application No. PCT/US2015/023789, titled: Devices for Targeted Delivery of Therapeutic Implants, dated Oct. 12, 2017.

\* cited by examiner

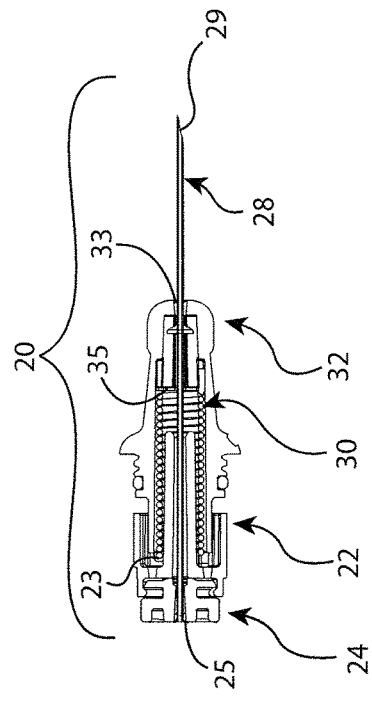
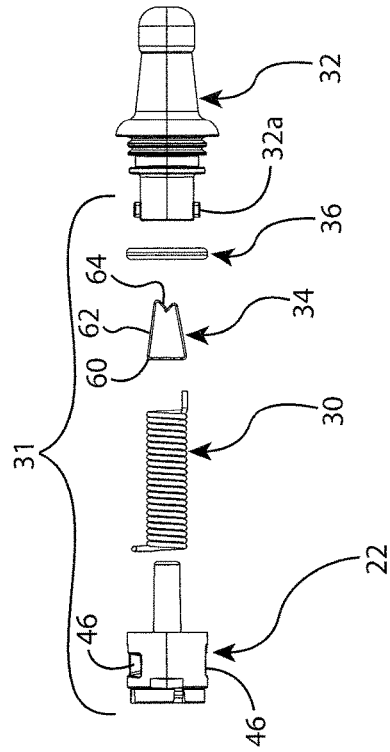
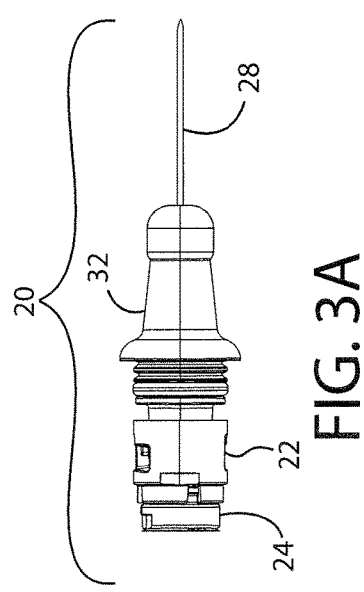
FIG. 3A
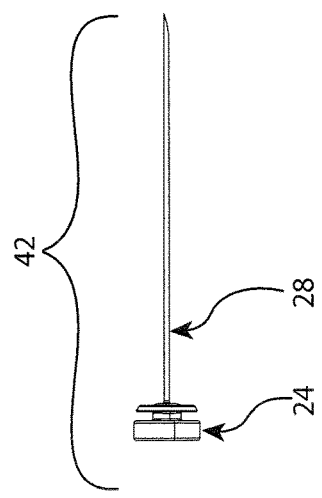
FIG. 3C

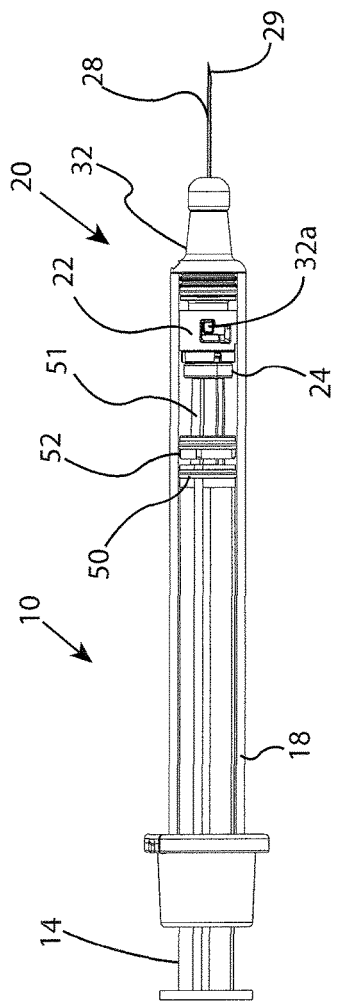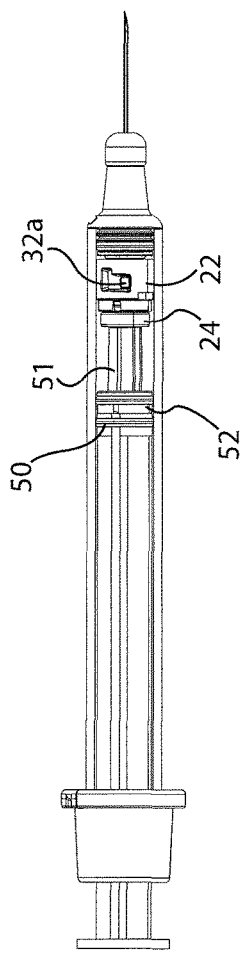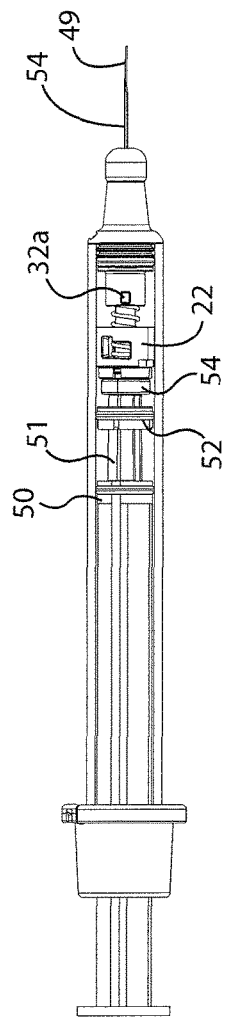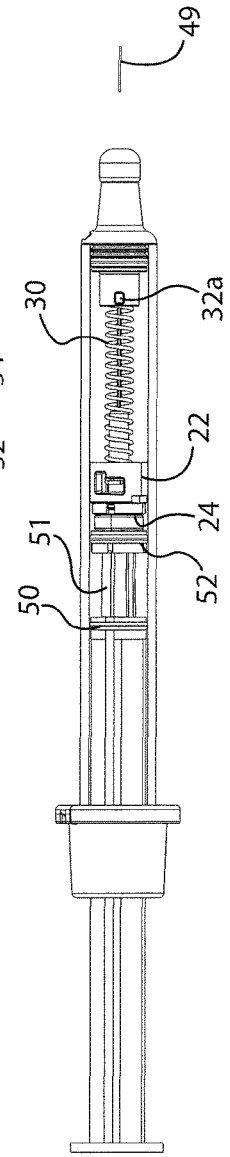
FIG. 7A
FIG. 7B
FIG. 7C
FIG. 7D

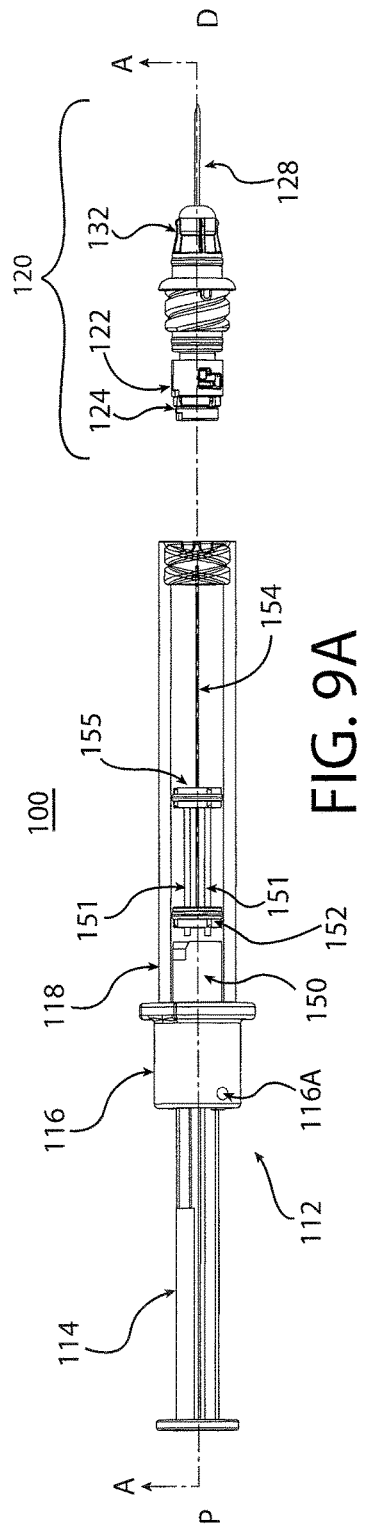
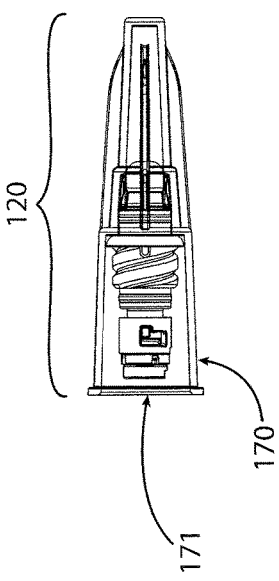
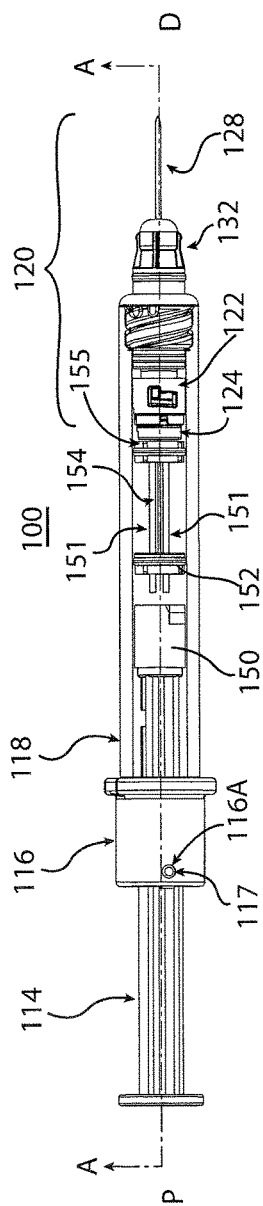
FIG. 9A
FIG. 9B
FIG. 9C

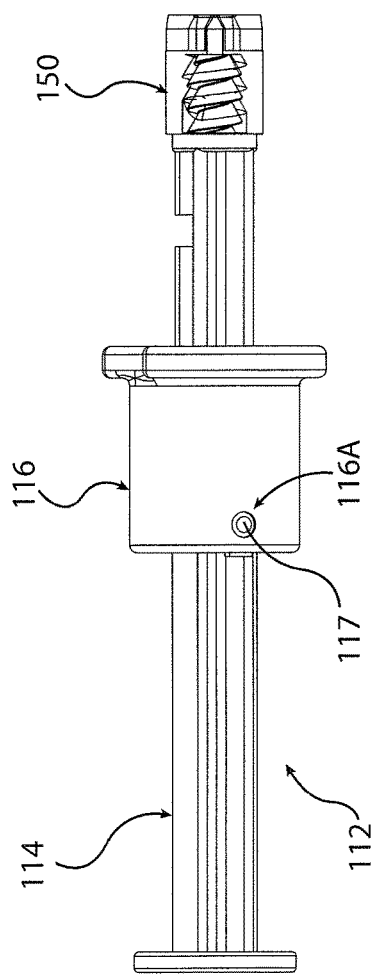
FIG. 10A
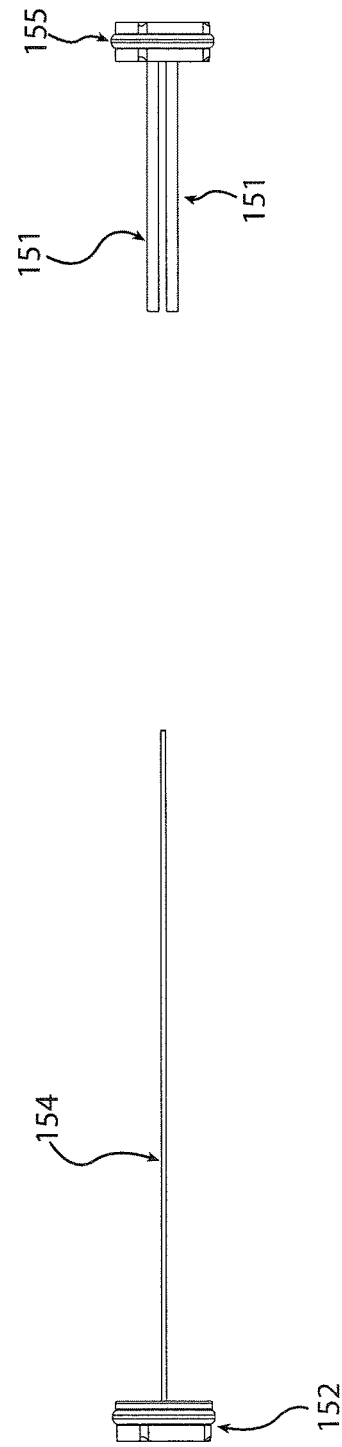
FIG. 10C
FIG. 10B

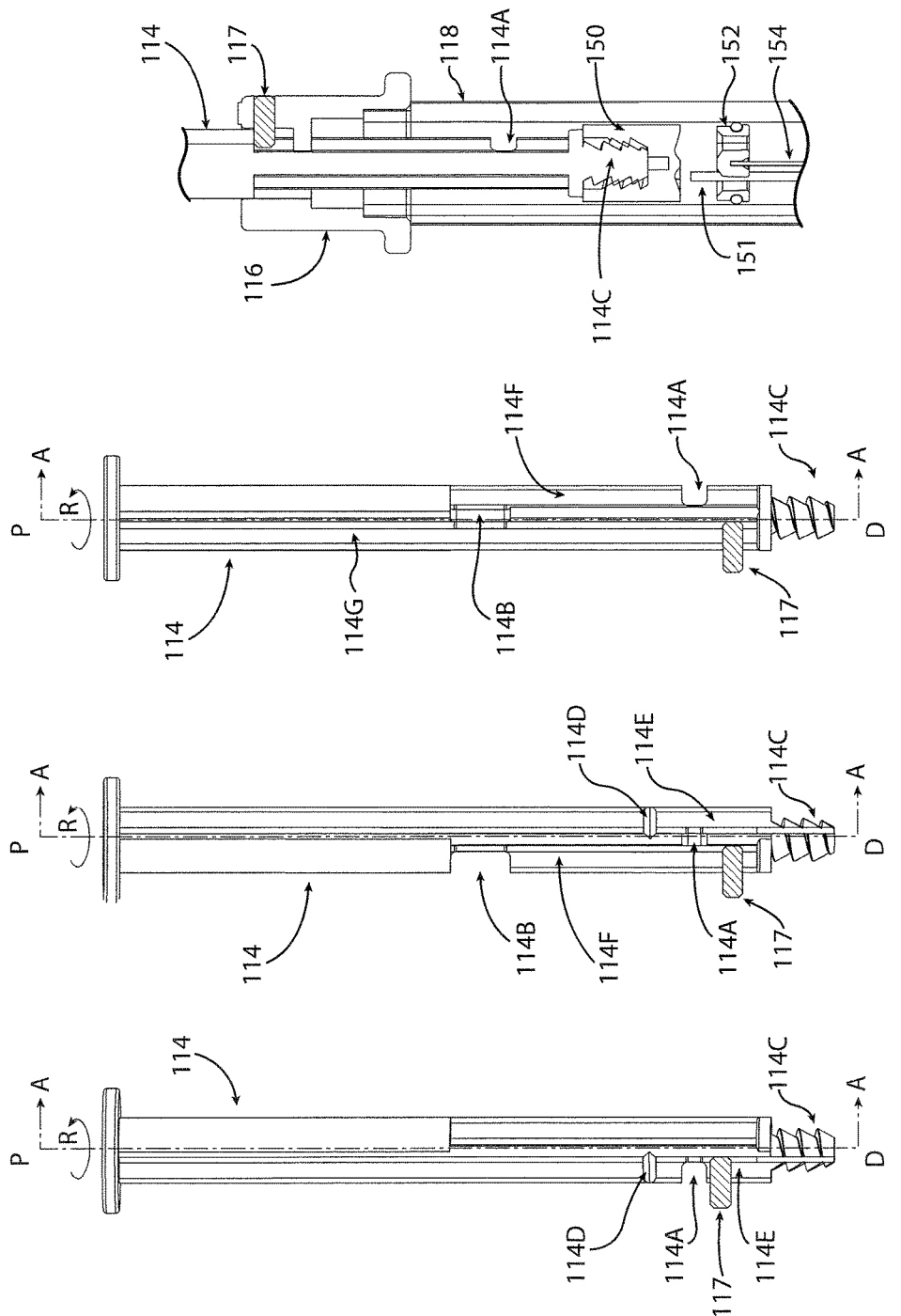

DEVICES FOR TARGETED DELIVERY OF THERAPEUTIC IMPLANTS

CROSS-REFERENCE TO RELATED APPLICATIONS

This application is a divisional patent application from U.S. patent application Ser. No. 13/775,155, which claims priority to U.S. Provisional Application No. 61/602,277, filed on Feb. 23, 2012; U.S. Provisional Application No. 61/639,898, filed on Apr. 28, 2012; U.S. Provisional Application No. 61/667,010, filed on Jul. 2, 2012; U.S. Provisional Application No. 61/677,186, filed on Jul. 30, 2012, and U.S. Provisional Application No. 61/767,369, filed on Feb. 21, 2013, all of which preceding applications are included by reference herein in their entirety for all purposes.

FIELD OF THE INVENTION

The present invention relates to devices for targeted delivery of a therapeutic implant (for example, pharmaceutical, radiation source, or medical device). More specifically, the embodiments of the present invention relate to a delivery system which is capable of depositing an implant to a specific location, syringes with retractable cannulas which facilitate delivery of drug implants, beads, pills, or capsules, methods for manufacturing such devices, and their methods of use.

BACKGROUND OF THE INVENTION

Recent therapies have revolutionized the way diseases such as Age-related Macular Degeneration, Diabetic Retinopathy, Diabetic Macular Edema, Prostrate Cancer, etc., are being treated. An aging population and increasing prevalence of diabetes are driving the demand for therapies used in the treatment of eye disorders. Several pharmaceutical companies are actively involved in developing new therapies in this space in addition to those that have drugs that have already been commercialized.

Currently, the most common drugs used to treat the wet form of age-related macular degeneration are angiogenesis inhibitors, which are typically injected into the vitreous portion of the eye (the clear jelly-like substance that fills the eye from the lens back to the retina). Most treatments require monthly injections. Injections are associated with some risk of contracting infections, such as endophthalmitis, in addition to patient inconvenience. Also, the need for clinicians to treat an increasing number of patients burdens the healthcare system as a whole.

Drug-implants or drug depots have the potential to increase the duration in which the drug remains active in the target site. This reduces the frequency with which patients would require treatment with injections; this consequently reduces the burden on the healthcare system and also reduces the likelihood of injection-related risks to the patient.

A device to deploy or deposit such an implant or depot should ideally be easy to use for the clinician, cause minimum discomfort and/or injury to the patient, and should not alter the drug delivery kinetics of the drug implant or depot. Current devices used to deploy/deposit implants typically require extensive training on part of the clinician, are painful (in addition to potentially being injurious) to the patients, and contribute to significant shear forces that could damage the implant. Physical damage to the implant may alter the drug delivery kinetics and consequently the drug's clinical efficacy and/or regulatory compliance. Current devices typically also do not allow for accurate positioning of the implant or depot.

BRIEF SUMMARY OF THE INVENTION

According to an aspect of the invention, there is provided a barrel adapter for a delivery syringe having a barrel and a plunger assembly adapted to move within the barrel. The adapter includes a barrel tip, a needle assembly, a stylet, and a needle retraction mechanism. The barrel tip is adapted to be sealingly engaged with a distal end of the barrel. The needle assembly is disposed at least partially within the barrel tip, and includes a needle and a needle hub through which the needle extends. The needle has a lumen, and is adapted to move from an injection position in which the needle extends from a distal end of the barrel tip to a retracted position in which the needle is disposed substantially completely within at least one of the barrel tip or the barrel. The stylet assembly includes a stylet and a stylet disc. The stylet is axially slidable, for example coaxial with the needle assembly and/or needle lumen, and at least partially disposed within the needle lumen. The stylet is proximally disposed and spaced from a distal tip of the needle when the needle is in the injection position. The needle retraction mechanism includes a biasing member and an actuable locking arrangement. The locking arrangement is disposed to maintain the biasing member in an energized position when the locking arrangement is locked and to release the biasing member when actuated. The locking arrangement is actuable by way of depression of the plunger assembly. The biasing member is disposed to provide relative motion of the needle and stylet from the injection position to the retracted position when the biasing member is released from the energized position. The relative motion includes moving the needle relative to the stylet, moving the needle with the stylet, and other relative motions of these components at one or more stages of operation from the injection position to the retracted position when the biasing member is released from the energized position.

According to another aspect of the invention, there is provided an automatically retractable implant delivery syringe. The delivery syringe includes a barrel having a distal end and a proximal end, a plunger assembly adapted to move within the barrel, a barrel tip sealingly engaged with a distal end of the barrel, a needle assembly, a stylet assembly, and a needle retraction mechanism. The needle assembly is disposed at least partially within the barrel tip and includes a needle and a needle hub through which the needle extends. The needle has a lumen. The needle is adapted to move from an injection position in which the needle extends from a distal end of the barrel tip to a retracted position in which the needle is disposed substantially completely within at least one of the barrel tip or the barrel. The stylet assembly includes a stylet and a stylet disc. The stylet is axially slidable and at least partially disposed within the needle lumen. The stylet is proximally disposed spaced from a distal tip of the needle when the needle is in the injection position. The needle retraction mechanism includes a biasing member and an actuable locking arrangement. The locking arrangement is disposed to maintain the biasing member in an energized position when the locking arrangement is locked and to release the biasing member when actuated. The locking arrangement is actuable via depression of the plunger assembly. The biasing member is disposed to provide relative motion of the needle and stylet from the injection position to the retracted position when the biasing member is released from the energized position. The relative motion includes moving the needle relative to the stylet, moving the needle with the stylet, and other relative motions of these components at one or more stages of operation from the injection position to the retracted position when the biasing member is released from the energized position.

According to yet another aspect of the invention, there is provided a method of assembling an automatically retractable safety syringe. The method includes the steps of disposing a plunger assembly to move within a barrel, sealingly engaging a barrel tip with a distal end of the barrel, disposing a needle assembly for movement within the barrel tip and the barrel between an injection position wherein a needle of the needle assembly extends from the barrel tip and a retracted position wherein the needle is disposed substantially completely within at least one of the barrel tip or the barrel, disposing a stylet of a stylet assembly, which includes the stylet and a stylet disc, at least partially within a lumen of the needle such that the stylet is axially slidable within the needle lumen and is proximally disposed spaced from a distal tip of the needle when the needle is in the injection position, and disposing a needle retraction mechanism including a biasing member and an actuable locking arrangement within the barrel, the locking arrangement being disposed to maintain the biasing member in an energized position when the locking arrangement is locked and to release the biasing member when actuated, the locking arrangement being actuable by depression of the plunger assembly, the biasing member being disposed to provide relative motion of the needle and stylet from the injection position to the retracted position when the biasing member is released from the energized position. The relative motion includes moving the needle relative to the stylet, moving the needle with the stylet, and other relative motions of these components at one or more stages of operation from the injection position to the retracted position when the biasing member is released from the energized position.

The present invention addresses shortcomings in current solutions and enables precise positioning of the implant or depot. For the purposes of this disclosure, the term "implant" will be used to include, collectively or individually, depots, implants, beads, pills, capsules, nodules, drug-eluting devices, dry or lyophilized drugs or treatments, or other forms of implants or the like. The present invention mimics the handling and use of parenteral drug injections and hence requires minimal to no training of the clinician. The present invention provides a delivery system which is capable of depositing an implant to a specific location, syringes with retractable cannulas which facilitate deployment of implants, methods for manufacturing such devices, and their methods of use. Embodiments of the present invention may provide enhanced patient comfort, patient safety, clinician convenience and regulatory compliance. The present invention addresses shortcomings in currently available solutions for targeted delivery of drug implants and enables precise positioning of the implant.

In the simplest form, the invention achieves this by mimicking parenteral drug injections, which involves the conventional use of a syringe and, hence, requires minimal or no training of the clinician. Embodiments of the present invention have broad applicability and can be used to deliver implants to numerous targeted locations within an anatomy, including to the eye, to the prostate, to the heart, to the brain, etc. The target locations could be, for example, organs or locations within a tissue (e.g., subcutaneous) or intra-tumoral. Embodiments can also be employed to deposit dry or lyophilized drugs. Embodiments of the present invention provide reliable needle retraction, for improved user safety, without requiring complex manufacturing processes.

Additionally, embodiments of the present invention provide configurations which utilize materials and components which are readily compatible with pharmaceutical applications and compliant with regulations for pharmaceutical use, many of which are increasingly considered off-the-shelf or standard components. Furthermore, the present invention provides components and devices which are visually similar to conventional syringes, which do not have needle retraction mechanisms, are ergonomic for end users such as a medical practitioners and self-administering patients, and provide highly desired integrated safety features.

Embodiments of the present invention leverage retraction of the needle which exposes the implant to its target region for implant deployment. Clinicians are familiar with operating conventional syringes and the ease of targeting provided by the same. By utilizing the fundamental aspects of such syringes, and by integrating a retraction mechanism, the inventors of the present invention have developed an intuitive, easy-to-use delivery system which utilizes a retractable needle syringe to accurately and safely deposit an implant.

In a first embodiment, the present invention provides a delivery system which includes a needle, a stylet, a retraction mechanism, an actuation mechanism, and contains an implant for delivery. The stylet, which is substantially coaxial to the needle, is placed in a lumen of the needle (e.g., the hollow bore of the needle). In one embodiment, the stylet may be partially overlapping the needle from the non-patient end (i.e., the proximal end). The implant is contained within the lumen of the needle between the stylet and patient-end of the needle (i.e., the distal end). An actuation mechanism, such as a plunger rod, may be utilized to actuate a retraction mechanism, causing the needle to retract. Initially, the stylet is stationary relative to the needle and retraction of the needle by the retraction mechanism exposes the implant in the target area for delivery. The stylet ensures that the implant does not follow the needle as it retracts. The stylet retracts with the needle only after the distal end of the stylet is past the distal end of the retracting needle. The sequence and timing of retraction of the stylet is such that retraction of the stylet is activated or triggered after the retraction of the needle, even though the same retraction mechanism may facilitate retraction of both components. A stylet disc that is proximal to the retraction mechanism may be utilized to ensure the desired sequence of retraction. The distance between the retraction mechanism and the stylet disc sets the sequence and/or timing of retraction of the stylet relative to the needle.

The components of the delivery system may be assembled as a barrel adapter for a syringe. Alternatively, the delivery system or aspects thereof may be formed as part of the syringe. The barrel adapter may be attached, affixed, or otherwise connected with a distal end of a syringe barrel. Accordingly, the barrel adapters include the components necessary for needle retention and retraction, and are configured to mate with standard barrels. The barrel adapter is configured to mate and be affixed, through a number of known methods, to the distal end of a barrel. In at least one embodiment, the barrel adapters are configured to mate with barrels that are substantially straight in cross-sectional profile (e.g., substantially parallel axially along at least a distal portion of the barrel), such as glass or plastic straight-barrels. The barrel adapters may be configured to mate with the barrel in a number of different ways. In a preferred embodiment, however, the barrel adapters are configured such that at least a proximal connecting portion is shaped to be mounted to, and reside within, the inner diameter of a distal portion of the barrel. This enables the barrel adapters to be flexibly adaptable to barrels of all types, particularly standard glass straight-barrels, thereby providing potential manufacturing advantages and operational cost-savings.

The barrel adapters of the present invention, therefore, simplify the assembly of needle retraction mechanisms with standard barrels to produce syringes with integrated needle safety features. The barrel adapters of the present invention enable selection and adaptation of varying needle assemblies with standard barrels. In other words, the design and configuration of the present invention allows a user to select a needle and/or needle sub-assembly of a particular design or dimensions and adapt it to a syringe barrel for drug delivery. Accordingly, the barrel adapters of the present invention enable further customization of the drug delivery device by the user or a pharmaceutical manufacturer, allowing them to employ the integrated retraction mechanism of the barrel adapter to any barrel to produce a delivery system syringe.

For example, the barrel adapters and needle assemblies may be configured to provide a number of different needle lengths. The user may then select the barrel adapter with their desired needle length and adapt it to a syringe to deliver the implant. Similarly, the user may select the desired stylet length appropriate for a given needle length to facilitate delivery of the implant to the desired depth. This flexibility of the present invention is particularly useful for drug delivery that is subcutaneous or intramuscular. The barrel adapters of the present invention may be configured to enable such flexibility.

One or more additional components may be utilized to provide this adaptive feature. For example, one or more connecting components may be utilized to connect the barrel tip of the barrel adapter to the barrel. In one such embodiment, one connecting component (such as a receiving component) may be fixedly mounted on a distal end of a glass barrel. The receiving component may directly receive and engage the barrel tip with the integrated retraction mechanism. Alternatively, the barrel adapter may include one or more additional connecting components (such as a mating component) which are used to engage the receiving component. Other optional components, such as elastomeric seals, which are known to one having ordinary skill in the art, may be desirable and incorporated into the device to facilitate the connection between the barrel adapter and the barrel and also create a sterile barrier for an assembled device.

In another embodiment, the present invention provides an implant delivery syringe adapted for delivery of an implant, the delivery syringe including a barrel, a plunger assembly, and a barrel adapter. The barrel adapter includes a barrel tip, a biasing member, a locking mechanism, a delivery system, and a needle assembly. The delivery system includes a stylet. The needle assembly may generally include a needle and a needle hub. In an initial configuration, the stylet may reside in the needle along with an implant for injection and delivery, as described above. The needle is configured to pass-through the needle assembly, locking mechanism, biasing member, and barrel tip such that, one end the needle is within the barrel and another end the needle passes through an aperture in the barrel tip. The barrel may be substantially cylindrical, having along its longitudinal axis a distal end for drug injection, a proximal end for injection control. The barrel adapter is configured to mate and be affixed, through a number of known methods, to the distal end of a barrel. The barrel adapter is capable of coupling or mounting to, or engaging with, a barrel of the delivery syringe.

In any of these embodiments of the barrel adapter, the biasing member is mounted, either fixedly or movably, generally within the barrel tip and the distal end of the barrel. The biasing member is biased to expand in the proximal direction and substantially along the longitudinal axis of the barrel.

The plunger assembly is adapted to initiate implant delivery and actuation of an actuable locking arrangement to cause retraction of the needle. The plunger assembly includes a plunger rod and may engage with or include a prong base. The plunger rod may be connected to the prong base by a number of different connections such as, for example, being screwed into the prong base, interference fit, etc. Alternately, the plunger rod may merely confront and move the prong base to initiate retraction of the needle. In yet another embodiment, the plunger rod may be unitarily formed with the prong base. Preferably, in at least one embodiment the prong base is a pre-formed aspect at the distal end of the plunger rod. The plunger assembly may be mounted at the proximal end of the barrel while the barrel adapter is mounted at the distal end of the barrel. The prong base may, for example, comprise of a plastic and/or elastomeric material. The prong base may be sized such that it provides a slidably contacting fit with an inner diameter of the barrel. Alternatively, the prong base may be spaced from the inner diameter of the barrel, so long as another element of the structure, for example, an element of the plunger rod, ensures relative positioning of the prong base. The prong base may have a one or more distally extending protrusions or prongs, which are complimentary to the features on the stylet disc. There is preferably sufficient clearance between these aspects to ensure that there is no or minimal interference or contact between the protrusions and the stylet disc. The stylet disc is attached to the proximal end of the stylet such that movement of the stylet disc causes movement of the stylet.

Upon actuation of the retraction mechanism, the needle assembly is caused to retract first. The needle hub, which is connected to the proximal end of the needle, is caused to retract by the disengaged locking mechanism and the expansion of the biasing member, thereby retracting the needle. As the needle hub retracts the prong base retracts. Because the stylet disc is allowed to freely travel over, or float relative to, the protrusions of the prong base, the stylet disc and the stylet are not initially caused to retract. Retraction of the stylet disc and the stylet only occur when the needle hub has translated axially in the proximal direction (i.e., retracted) at a distance far enough to contact the stylet disc, at which point all of the components (including needle and stylet) are caused to retract together. The spacing of the stylet disc from the needle hub ensures that retraction of the stylet disc and stylet only occur after the distal end of the stylet is distal to, or in-line with, the distal end of the needle such that the implant is exposed and delivered to the target location before retraction of the stylet. In at least one embodiment, the spatial arrangement of the stylet disc and the needle hub enables the lag in retraction of the stylet relative to the needle.

One or more embodiments of the present invention may optionally include certain standard components. For example, the barrel adapter configurations and syringe devices of the present invention may include one or more O-rings. In at least one embodiment, one or more O-rings are employed to seal the barrel tip within the barrel and/or to ensure a sterile environment and container integrity within the barrel, and/or to enable axial translation of the device components; Additionally or alternatively, the barrel adapter may include one or more controlling members to facilitate the control of the rate of retraction. Similarly, the barrel adapter may include one or more needle blocks, such as clips, flaps, flanges, or the like, which function to prevent the needle from being translated or protruding out of the barrel through the aperture of the barrel tip after the retraction mechanism has been initiated or completed. Furthermore, the syringe may include one or more components for aesthetics, ease-of-use, or other purposes. For example, one or more embodiments of the present invention may include a finger flange.

The novel delivery system, barrel adapter, and implant delivery syringe designs of the present invention obviate the need to have a particular barrel shape or configuration for mounting a needle assembly thereto. Another desirable feature of the present invention is to provide a relatively simplified needle assembly which comprises fewer components, thereby providing a user-friendly and safe retractable syringe while keeping manufacturing costs to a minimum and/or facilitating mass distribution of retractable syringes. Embodiments of the present invention also provide configurations which allow the use of standard, commercially-available components, which may reduce overall manufacturing costs, streamline assembly processes, and avoid regulatory concerns often associated with non-standard materials and components. Additionally, the invention provides efficient delivery of implants in an intuitive, easy-to-use and accurately targetable configuration. The invention also integrates one or more locking systems to prevent or at least minimize tampering, syringe re-use, needle stick injury, and/or prevent injury to the target organ or tissue.

Accordingly, in yet another embodiment the present invention provides a method for assembling an implant delivery syringe having a barrel adapter, a plunger assembly, and a barrel having a longitudinal axis. The method includes the steps of: assembling the barrel adapter which includes a barrel tip, a biasing member, a locking mechanism, a stylet, and a needle assembly; mounting the barrel tip to a distal end of the barrel; and mounting the plunger assembly having a prong base and a plunger rod to a proximal end of the barrel. The barrel adapter may be fixedly affixed, such as by glue, to the distal end of the barrel. The method for assembling the delivery syringe may further include the step of positioning an implant in the needle.

The plunger assembly may be movably mounted to the proximal end of the barrel by first inserting the prong base into the barrel and then inserting the plunger rod. Alternatively, the prong base may be inserted into the distal end of the barrel with the barrel adapter. The plunger rod may optionally be coupled to into the prong base by screw connection or another known method of connection. Alternatively, the plunger rod and prong base may be unitarily formed and inserted into the proximal end of the barrel.

In at least one embodiment, the barrel adapter is in a compressed configuration prior to mounting into the barrel. For example, the biasing member may be compressively engaged, such as in an energized stage, between the locking mechanism and the barrel tip prior to mounting the barrel adapter into the barrel. In another embodiment, these components may be mounted into the barrel prior to compressing and locking the biasing member into place. Accordingly, the method may further include the steps of compressing the biasing member and locking the locking mechanism into an engaged and energized position after the mounting of the barrel adapter to the barrel. It is contemplated that the plunger assembly may be utilized to compress the biasing member and lock the locking mechanism in some embodiments.

In another embodiment, the present invention relates to a method of use for a delivery syringe having a barrel adapter, a plunger assembly, and a barrel having a longitudinal axis. The barrel adapter, which may be mounted to a distal end of the barrel, includes a barrel tip, a biasing member such as a compression spring, a locking mechanism, a delivery system, and a needle assembly; wherein the components of the barrel adapter reside substantially within the barrel tip and the distal end of the barrel. The plunger assembly, which may be mounted to a proximal end of the barrel, includes a plunger rod, and confronts or includes a prong base from which at least one prong extends. The barrel adapter may be fixedly affixed, such as by glue, to the distal end of the barrel. The plunger assembly may be movably mounted to the distal end of the barrel by first inserting the prong base into the barrel and then inserting the plunger rod into the prong base by screw connection or another known method of connection. Alternately, the plunger rod may be advanced to a position to confront the prong base, which may be positioned within the barrel from either end of the barrel.

In the method of use, the syringe, which includes the stylet and implant in their initial configurations within the needle, may be injected into a target location for delivery of the implant. An actuation mechanism, such as the plunger rod and prong base of the plunger assembly, may be utilized to activate a retraction mechanism which, in at least one embodiment, disengages the locking mechanism from its locked state. The locking mechanism initially retains the biasing member in a stored and energized configuration, which is then permitted to expand upon disengagement of the locking mechanism. The expansion of the biasing member causes retraction of the needle. Initially, the stylet is stationary relative to the needle; upon activation, retraction of the needle by the retraction mechanism exposes the implant in the target area for delivery. The stylet ensures that the implant does not follow the needle as it retracts. In this way, the implant is delivered as the needle retracts. Once the distal end of the retracting needle is in-line with or passes the distal end of the stylet, the stylet may retract with the needle. Suitably, the stylet is caused to retract with the needle once the implant has been exposed and delivered to the target area for delivery.

The method of use includes the steps: injecting the needle into a target location; depressing the plunger assembly to trigger the locking mechanism to release the biasing member from its energized state, contact between the biasing member and the needle assembly causing the needle assembly to retract into the barrel while initially maintaining the stylet stationary relative to the needle; exposing and deploying the implant to the target location; retracting the stylet after the distal end of the stylet is beyond, in the distal direction, the distal end of the needle. In a further embodiment, a locking clip may lock the needle and stylet after both components have been retracted substantially into the barrel and/or barrel tip to prevent re-use of the delivery syringe. In at least one embodiment, the locking mechanism may include an interface on the barrel tip which engages the locking mechanism. Upon activation by the user, the needle hub may be employed to initiate the release of the locking mechanism from its engagement with the barrel tip. By releasing the locking mechanism from the barrel tip, the biasing member is allowed to expand causing the needle assembly to retract in the proximal direction substantially along a longitudinal axis of the barrel. In some embodiments of the present invention the entire needle assembly is caused to retract, while in other embodiments only certain components thereof, including the needle, are caused to retract upon release of the locking mechanism and activation of the biasing member. Similarly, in some embodiments of the present invention the locking mechanism is caused to retract with the needle assembly while in other embodiments the locking mechanism remains substantially stationary but enables the needle assembly, or components thereof, to move.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, embodiments of the present invention may include one or more additional components which may be considered standard components in the industry of medical devices. The components, and embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 3A shows an enlarged side view of a barrel adapter according to an embodiment of the present invention;

FIG. 3B shows a cross-sectional side view of the barrel adapter of FIG. 3A along a longitudinal axis (cross-hatching being eliminated in the interest of clarity);

FIG. 3C shows a partially exploded side view of the barrel adapter of FIG. 3A, separating the needle assembly from the other components of the barrel adapter;

FIGS. 7A-7D show side elevational views of a delivery syringe including a barrel adapter according to an embodiment of the present invention, as the syringe progresses through the stages of needle injection, needle retraction activation, implant delivery, and stylet retraction;

FIG. 9A shows a side elevational view of a delivery syringe including a barrel adapter with a screw-fit connection according to another embodiment of the present invention;

FIG. 9B shows a side elevational view of the barrel adapter shown in FIG. 9A contained within a needle cap (shown as a transparent component for clarity), according to another embodiment of the present invention, such as may be utilized for packaging, transport, and/or assembly;

FIG. 9C shows a side elevational view of the delivery syringe and barrel adapter shown in FIG. 9A in an assembled configuration;

FIG. 10A shows an enlarged side elevational view of a plunger assembly, according to at least one embodiment of the present invention;

FIG. 10B shows an enlarged side elevational view of a stylet assembly having a stylet and a stylet disc, according to at least one embodiment of the present invention;

FIG. 10C shows an enlarged side elevational view of a stylet guide and one or more protrusions or prongs, according to at least one embodiment of the present invention;

FIGS. 11A-11C show side elevational views of a plunger rod, according to at least one embodiment of the present invention, rotated around axis A at 90 degree intervals, respectively, as indicated by arrow R;

FIG. 12 shows an enlarged fragmentary cross-sectional view (cross-hatching being eliminated in the interest of clarity) of the embodiment of the delivery syringe shown in FIG. 9A;

DETAILED DESCRIPTION OF THE INVENTION

Figure 1:
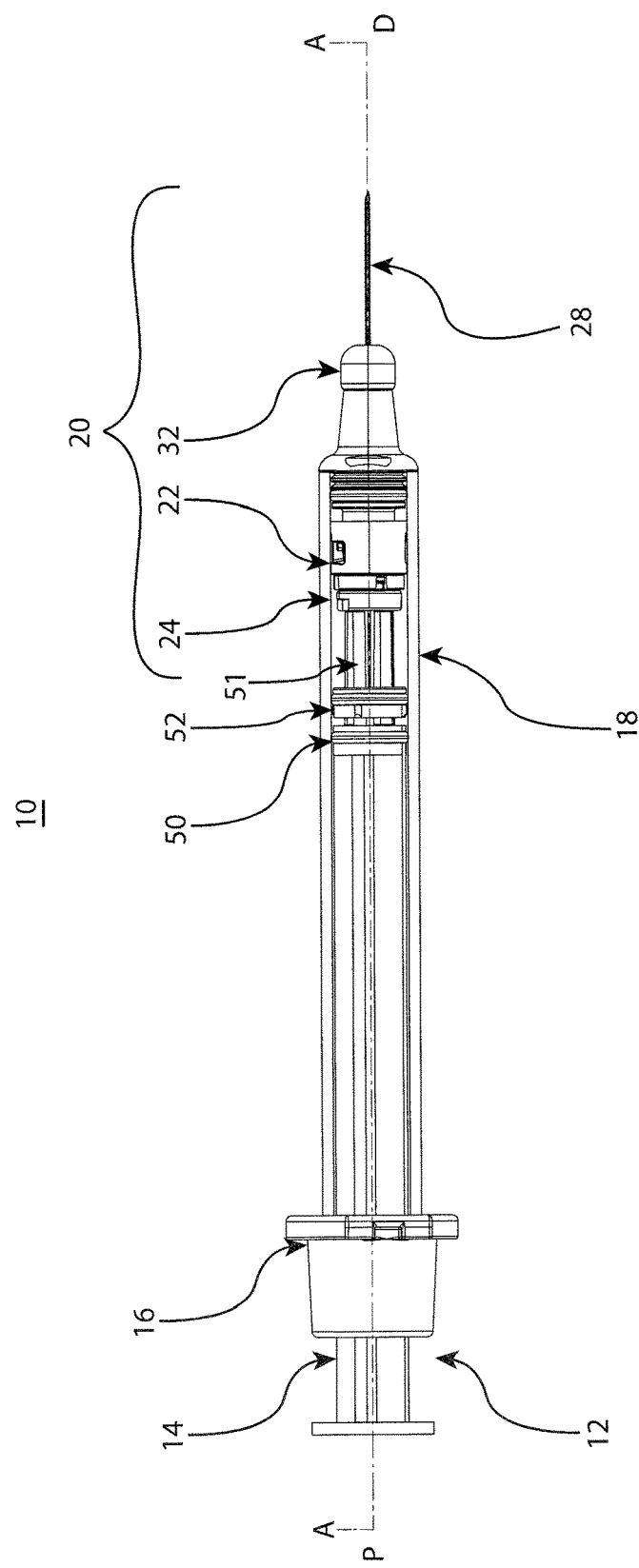
FIG. 1 is a side elevational view of a first embodiment of a delivery syringe including a delivery system according to the present invention.

Embodiments of the present invention leverage retraction of the needle to deposit an implant. The implant could be, for example, drug eluting or could be a radiation emitting bead. For the purposes of this disclosure, the term "implant" will be used to include, collectively or individually, depots, implants, beads, pills, capsules, nodules, drug-eluting devices, dry or lyophilized drugs or treatments, or other forms of implants or the like.

Clinicians are familiar with the ease of targeting and operation provided by conventional syringes. By utilizing the fundamental aspects of such syringes, and by integrating a retraction mechanism, the inventors of the present invention have developed an easy-to-use delivery system which utilizes a retractable needle syringe to accurately and safely deliver or deploy an implant. The implant is deposited at the point at which the needle is placed within the target location. This allows for accurate placement of the implant and makes the placement of the needle more deterministic of the delivery location than in existing devices for implantation. Existing devices for implantation generally utilize a means for pushing an implant out of a cannula for depot or implant delivery. Such devices are often inaccurate because the user customary desires to position the tip of the cannula at the targeted location. Once the tip of the cannula is at the target location, pushing the implant out of the cannula by conventional methods results in the inaccurate delivery of the implant. To compensate for this inaccuracy, users may choose to "short position" the tip of the cannula an estimated distance from the target location so that the implant is pushed closer to the target location. The embodiments of the present invention utilize a fundamentally different approach which greatly increases the accuracy of targeted delivery and is easy-to-operate for users. By positioning the implant at the tip of the syringe needle, inserting the syringe needle to the desired target location, and then withdrawing or retracting the syringe needle away to deploy the implant, the accuracy of implant delivery to the targeted location is greatly improved than by conventional means for implantation. Additionally, because the position of the implant does not change throughout the implantation process, thus eliminating any need for calculation or estimation by the user, the embodiments of the present invention are easy-to-operate for users. Furthermore, the embodiments of the present invention provide desirable safety features because the syringe needle is retracted substantially fully into the barrel and/or barrel tip of the implant delivery syringe, thereby eliminating the risk of needle-stick injuries.

In a first embodiment, the present invention provides a delivery system which includes a needle, a stylet, a retraction mechanism, an actuation mechanism, and an implant for delivery. The stylet, which is substantially coaxial to the needle, is placed in a lumen of the needle (e.g., the hollow bore of the needle). In one embodiment, the stylet may be partially overlapping the needle from the non-patient end (i.e., the proximal end). The implant is placed in the lumen of the needle between the stylet and patient-end of the needle (i.e., the distal end). An activation mechanism, such as a plunger rod, may be utilized to activate a retraction mechanism, causing the needle to retract. Initially, the stylet is stationary relative to the needle and retraction of the needle by the retraction mechanism exposes the implant in the target area for delivery. The stylet ensures that the implant does not follow the needle as it retracts. The stylet retracts with the needle only after the distal end of the stylet is past the distal end of the retracting needle. The sequence and timing of retraction of the stylet is such that retraction of the stylet is activated or triggered after the retraction of the needle, though the same retraction mechanism may be used to retract both components. A stylet disc that is proximal to the retraction mechanism may be utilized to ensure the desired sequence of retraction. The distance between the retraction mechanism and the stylet disc set the sequence and/or timing of retraction of the stylet relative to the needle.

Embodiments of the present invention provide accurate implant deployment mechanisms utilizing needle retraction without requiring complex manufacturing processes. Embodiments of the present invention provide for a relatively simplified syringe assembly which comprises fewer components, thereby providing a user-friendly and safe implant deployment syringe while keeping manufacturing costs to a minimum. The novel barrel adapters of the present invention are notably able to be adapted to primary drug barrels of varying configurations and materials such as, preferably, straight-barrel glass or plastic barrels to provide integrated needle assemblies and retraction mechanisms to the barrel. As such, the adaptable implant deployment and needle retraction mechanisms of the present invention may be flexibly attached, affixed, mounted, or otherwise mated to standard barrels, such as straight-glass barrels. The barrel adapters may be configured to mate with the barrel in a number of different ways, however, in a preferred embodiment, the barrel adapters are configured such that at least a proximal connecting portion is shaped to be mounted to, and reside within, the inner diameter of a distal portion of the barrel. As such, the barrel adapter may be connected to a standard straight-barrel syringe by having at least a proximal portion of the adapter inserted into and attached, affixed, mounted, or otherwise mated to the distal end of the barrel. The barrel adapter may be connected to the barrel by, for example, an interference fit assembly, a snap-fit assembly, and/or a screw-fit assembly. As would be appreciated by one having ordinary skill in the art, any of these methods of connection may also include a locking feature to, for example, inform the user that the connection has been made and prevent disconnection of the barrel adapter from the delivery syringe during or after use. In at least one embodiment of the present invention, as detailed further herein, the barrel adapter may be connected to the barrel via a screw-fit assembly. The novel barrel adapter designs of the present invention therefore obviate the need to have a particular barrel shape or configuration for mounting a needle assembly thereto. This may substantially reduce manufacturing costs, especially those associated with the manufacture of specifically tailored glass barrels. The novel barrel adapters of the present invention can be mounted to, for example, straight glass or plastic barrels thereby simplifying the manufacturing process and costs associated with the manufacture of more complex barrel shapes.

The barrel adapters of the present invention may be selectable at the time of use or pre-attached to the barrel during manufacturing. In the selectable option, the design and configuration of the present invention allows a user to select a needle and/or needle assembly of a particular design or dimensions and adapt it to a syringe barrel for drug depot or implant delivery. For example, the barrel adapters and needle assemblies may be configured to provide a number of different needle lengths or thicknesses. The user may then select the barrel adapter with their desired needle dimensions and adapt it to a syringe to deliver the implant. In embodiments shown in FIGS. 1 and 2, the barrel adapter is directly mounted to the barrel. One or more additional components may be utilized to provide this adaptive feature. For example, one or more connecting components may be utilized to connect the barrel tip of the barrel adapter to the barrel. In one such embodiment, one connecting component (such as a receiving component) may be fixedly mounted on a distal end of a barrel. The receiving component may directly receive and engage the barrel tip with the integrated retraction mechanism. Alternatively the barrel adapter may include an additional connecting component (such as a mating component) which is used to engage the receiving component. As described above and detailed further herein, in at least one embodiment of the present invention the barrel adapter may be connected to the barrel via a screw-fit assembly with both the barrel adapter and the barrel having corresponding male and female screw pitch portions or components. Other optional components, such as elastomeric seals, which are known to one having ordinary skill in the art, may be necessary and incorporated into the device to facilitate the connection between the barrel adapter and the barrel. The barrel adapters, while including essentially the same components regardless of needle dimensions, may be customized to facilitate implant deployment and the complete retraction of the needle and stylet into the barrel. For example, longer biasing members (e.g., longer springs) may necessarily be selected or modified to facilitate retraction of a longer needle, as would be readily appreciated by one ordinarily skilled in the art. Similarly, a longer or thicker stylet may be necessary when utilizing a longer or thicker needle. Such dimensions may also be adjusted, for example, to facilitate delivery of a longer or shorter implant initially retained within the needle for delivery.

Embodiments of the present invention provide configurations which may also utilize materials and components which are readily employable for pharmaceutical use, many of which are increasingly considered off-the-shelf or standard components. Specifically, the materials used may be those which have low extractables content. This reduces overall manufacturing costs, streamlines assembly processes, and avoids unnecessary regulatory concerns often associated with the use of non-standard materials and components. Additionally, the present invention provides components and devices which are aesthetically-similar to conventional syringes which do not have needle retraction mechanisms, are ergonomically attractive to end-users such as a medical practitioners and self-administering patients, and provide highly desired integrated safety features. These embodiments, accordingly, provide novel and cost-efficient components and devices which are readily integrated into existing manufacturing processes. These aspects of the present invention may provide highly desired functional and aesthetic characteristics, and may be modified to produce a range of different configurations.

The syringes of the present invention enable targeted delivery of drug implants with integrated safety as they prevent accidental exposure to the needle, as is common with needle stick injuries. As described above and detailed in the figures, a user may utilize the delivery syringes of the present invention to perform the stages of drug implant delivery, including: needle injection, needle retraction activation, implant delivery, and stylet retraction. By integrating one or more locking systems to prevent or at least minimize syringe re-use and/or needle stick injury, embodiments of the present invention provide highly desirable products which are cost-efficient to manufacture and easy-to-use by medical practitioners and self-administering patients. Such locking systems may include, for example, needle retraction mechanisms and/or arrangements that block a retracted needle from again extending from the end of the syringe. The novel features and functionality of the barrel adapters and syringes of the present invention provide a number of safety advantages to the user. For example, the locking mechanism may be configured to provide visual, audible, and/or tactile feedback to the user that the drug dose has been fully delivered, the retraction mechanism has been activated, the needle has been retracted, and that the syringe is safe for disposal.

The components of the present invention may also be configured such that there is increased destruction of the components, and the syringe overall, at the end of use. Such integrated safety and destruction prevents the reusability of the syringe and increases the safety profile of the device. For example, an optional needle block may be configured to prevent the needle from translating in the proximal direction out of the barrel tip after needle retraction. Depression of the plunger rod and axial translation of the needle in the proximal direction, in this configuration, will result in the needle becoming bent within the barrel as a force is applied by the user.

Another safety feature enabled by the present invention is the ability to control the rate of retraction of the needle. Controlled needle retraction prevents injury to the patient after the drug dose has been delivered. This can be facilitated by active components, such as one or more friction members limiting the rate of expansion of the biasing member upon retraction activation, or by passive components, such as the selection of biasing members which have slower expansion. In the embodiments shown in FIGS. 1 and 2, the retraction is controlled by plunger rod and prong base. Upon activation of needle retraction, the user is still in contact and applying force to the proximal end of the plunger rod. As the biasing member is caused to expand, it imposes an axial force in the proximal direction to retraction the needle and/or needle assembly. This action conveys the force to the prong base, which is in contact with the needle hub upon retraction, and the plunger rod. The friction caused by the needle hub and the prong base against the interior of the barrel limits the rate of retraction of the needle assembly. As the user reduces the force they apply on the plunger rod, they can also control the rate of retraction. This controlled retraction is highly desired by syringe users as it increases the safety and reduces the pain felt to the patient.

Embodiments of the present invention are detailed further herein with respect to the attached figures. It is to be understood that these are merely non-limiting embodiments and that other similar embodiments are within the contemplation of the present invention and within the breadth and scope of the present disclosure.

As used herein to describe the delivery system, syringe, barrel, barrel adapter, or any of the relative positions of the components of the present invention, the terms "axial" or "axially" refer generally to a longitudinal axis "A" around which syringe or barrel is preferably formed although not necessarily symmetrically there-around. The term "radial" refers generally to a direction normal to axis A. The terms "proximal," "rear," "rearward," "back," or "backward" refer generally to an axial direction away from the needle end to be injected into the patient (identified generally as "P" in FIG. 1). The terms "distal," "front," "frontward," "depressed," or "forward" refer generally to an axial direction towards the needle end to be injected into the patient (identified generally as "D" in FIG. 1). It is to be understood that the term "spring" is used herein to suggest a biasing member, such as a substantially spiral-wound coil, that may be compressed and allowed to expand in a given direction. While a spring such as the arrangement discussed and utilized in embodiments detailed herein may be utilized, it is within the contemplation of the present invention that other types of biasing members may be readily employed for the same purpose while remaining within the breadth and scope of the present invention. For example, springs such as compression springs, torsion springs, constant force springs, extension springs, leaf springs, and combinations of the same or different types of springs or other structure may be utilized within the scope of the present invention, as would be understood by an ordinarily skilled artisan. Additionally or alternatively, biasing members other than springs may also be employed for similar purposes. Non-limiting examples of biasing members include a spring, elastic or other device for storing releasable energy. In at least one embodiment, however, the biasing member is preferably a spring, such as a compression spring.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be resoftened to their original condition by heat; thermosetting polymers cannot. As used herein, the term "plastic" refers primarily to moldable thermoplastic high polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or rubbery elastomers that are approved for use in applications where they are in direct contact with therapeutic liquids that can interact with plastic or that can be degraded by substituents that could otherwise enter the liquid from plastic. As used herein, the term "elastomer," "elastomeric" or "elastomeric material" refers primarily to crosslinked thermosetting rubbery polymers that are more easily deformable than plastics, but that are approved for use with pharmaceutical grade fluids and are not readily susceptible to leaching or gas migration. As used herein, the term "fluid" refers primarily to liquids, but can also include suspensions of solids dispersed in liquids, and gasses dissolved in or otherwise present together within liquids inside the fluid-containing portions of syringes.

Additionally, the devices of the present invention utilize materials that are substantially non-reactive with therapeutic fluids or drugs, and are suitable for use in pharmaceutical grade applications. Such novel configurations and delivery syringes of the present invention provide increased stability and shelf-life parameters to the implant and drug delivery devices. Additionally, known methods and materials may be modified and/or utilized to the keep the drug implant in place during storage and transit. Generally, a range of biodegradable materials, including polymers, may be utilized to plug the distal end of the needle to retain the implant prior to needle injection and implant deployment. For example, micro-deposition of polymer (PLGA, CAHP, and the like) may be utilized for this purpose. The nature of polymer used may depend on the target site, e.g., the choice of water-soluble polymers in an aqueous or water-containing site. Similarly, the plug may be composed of the same material as the implant, e.g., the same polymer may be utilized to coat of enclose the implant as is used for the plug. The implant may be placed into the needle prior to, or after, plugging the distal tip of the needle, as may be necessary to facilitate assembly and manufacturing of the barrel adapter and delivery syringe. For example, the implant may be placed into the needle prior to plugging the distal tip of the needle when the device assembly requires implant insertion from the distal end. This may be necessary, for example, if the barrel adapter is fixed to the barrel prior to insertion of the implant. Alternatively, the implant may be placed into the needle after plugging the distal tip of the needle. This may be utilized, for example, when the implant is inserted into the barrel adapter prior to assembly of the barrel adapter to the barrel of the delivery syringe. A number of methodologies may be utilized to position the plug within the needle cannula. For example, the plug may be inserted into the cannula from either the distal or proximal ends of the needle cannula. Alternatively, the plug may be formed within the needle cannula. For example, a liquid polymer may be dispensed, dispersed, or otherwise caused to enter the needle cannula wherein it is caused or permitted to at least partially solidify or become a gel to form a substantially static plug (i.e., prevent movement until desired by user). A number of other possible methodologies may readily be appreciated by one having ordinary skill in the art.

Similarly, surface treatment of stylet tip is envisioned to prevent non-specific and specific adhesion of the implant to the stylet and may be performed in any order of operations with reference to the assembly and manufacturing of the barrel adapter and delivery syringe. For example, treatments to maximize hydrophilicity of the stylet tip surface may be utilized to treat the stylet and/or coat the stylet tip. Generally, the materials utilized for the barrel adapter components, including the barrel tip, may be materials which prevent non-specific and specific adhesion so that the stylet and other components are permitted to function properly with regard to the operation of the embodiments of the present invention. Such materials, and the selection thereof, may readily be appreciated by one having ordinary skill in the art.

One or more embodiments of the present invention may further include certain standard components. For example, the barrel adapter configurations and syringe devices of the present invention may include one or more O-rings. In at least one embodiment, one or more O-rings are employed to seal the barrel tip within the barrel and/or to ensure a sterile environment and container integrity within the drug chamber of the barrel. Additionally or alternatively, the barrel adapter may include one or more controlling members to facilitate the control of the rate of retraction. Similarly, the barrel adapter may include one or more needle blocks, such as clips, flaps, flanges, or the like, which function to prevent the needle and stylet from being translated or protruding out of the barrel through the aperture of the barrel tip after the retraction mechanism has completed.

Furthermore, the delivery syringe may include one or more components for aesthetics, ease-of-use, or other purposes. For example, one or more embodiments of the present invention may include a finger flange, as will be understood by those of skill in the art. The finger flange may be pre-formed along any portion of the barrel or delivery syringe, or may be a separate component that is connected to or affixed to the barrel or delivery syringe. In at least one embodiment, the finger flange is a preformed component at the proximal end of the barrel. The finger flange may be configured to allow a user to rest their pointer and middle fingers on the flange, and may provide a leverage interface when the user is depressing the plunger with their thumb for injection of the drug. The position, shape, number, and materials for such components may vary, as would be readily appreciated by a skilled artisan, to meet any number of desired characteristics.

Similarly, while the components of the barrel adapter and the delivery syringe are described herein as separate components, it is within the contemplation of the present invention that certain groups of these components may be combined to form a single component capable of performing the functions of the individual components. As described above, for example, in at least one embodiment, if a needle seal is provided, the needle hub and needle seal may be one unified component that provides a dual function. Additionally, as would be appreciated by one having ordinary skill in the art, the components of the delivery syringes may be manufactured as unitarily formed components, or as individual or single components. As described above, the finger flange may be a component that is pre-formed, during the manufacturing process, as a part of the barrel itself. Accordingly, in at least one embodiment, the finger flange may be a glass finger flange extension of the barrel. Furthermore, while the components of the barrel adapter are described herein as separate components, they may be unified components having multiple functions. For example, the prong base may be a part of the plunger or a separate component from the plunger. Similarly, the protrusions or prongs may be extensions of the prong base or may be separate components from the prong base, as is described further herein. The configuration of the components and their assembly may vary based on the assembly process, the device parameters, and other desired characteristics.

Figure 2:
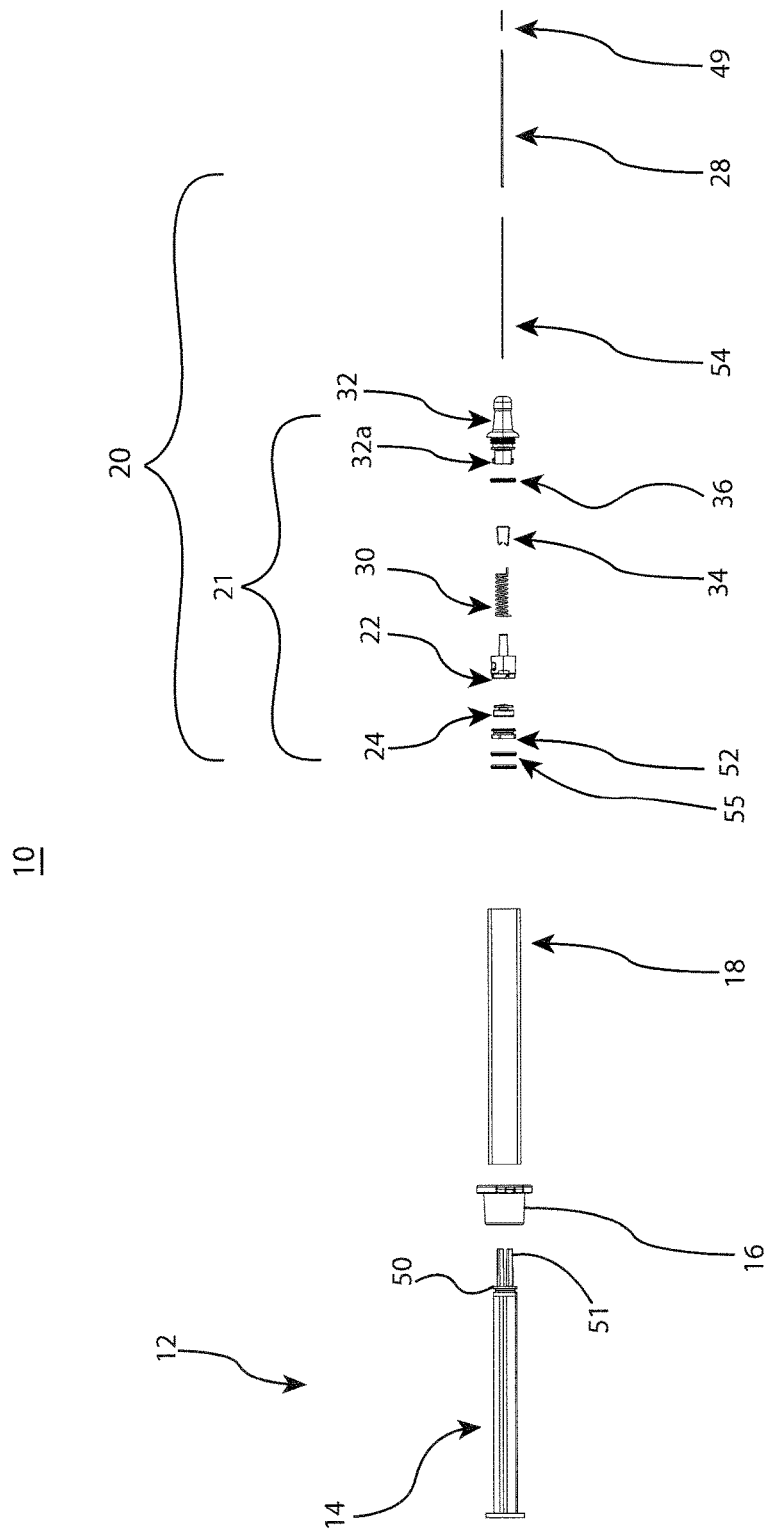
FIG. 2 is an exploded view, along a longitudinal axis, of the embodiment shown in FIG. 1.

FIG. 1 shows an isometric view of one embodiment of a delivery syringe 10, according to the present invention. FIG. 2 shows an exploded view of the delivery syringe 10, and its components, shown in FIG. 1. In accordance with the invention, a barrel adapter 20 is provided for attachment to a syringe barrel 18 having a plunger assembly 12. As an advantage of the embodiments of the present invention, the barrel tip 32 of the barrel adapter 20 may be configured to mate with any standard barrel 18 by any appropriate method. The barrel 18 may be a plastic barrel, a glass barrel, or made of any other known material for use in medical devices. The barrel 18 may be tapered, non-cylindrical, or substantially straight. In an embodiment preferred for manufacturing purposes, the barrel 18 is a straight barrel glass cylinder. In one or more embodiments, the barrel 18 may be, for example, a standard, off-the-shelf component, providing valuable manufacturing efficiencies and operational cost-savings. There may additionally be provided a barrel cap 16, which may inhibit or prevent the separation of the plunger assembly 12 from the barrel 18 once the delivery syringe 10 is assembled. The barrel 18 or the barrel cap 16 (as illustrated) may include a finger flange.

Embodiments of the present invention also enable significant other advantages in the marketplace for delivery syringes. For example, one or more embodiments can utilize standard components, such as standard plunger rods, barrels, barrel caps, and rigid needle shields, thereby greatly reducing the need for specially-tailored or injection molded components. For example, some embodiments the delivery syringe 10 may utilizes a standard plunger rod 14 and a rigid needle shield (not shown), among other possible standard components. If provided, the seals used herein may be an ethylene tetrafluoroethylene (ETFE) coated rubber stopper/seal, such as that which is readily-available under the trade name "FluroTec" from West Pharmaceutical Services, Inc., of Lionville, Pennsylvania of under the trade name "Omniflex" from Datwyler Pharma Packaging of Belgium. Other components may similarly be standard, off-the-shelf components, providing a great advantage of embodiments of the present invention. This advantage of embodiments of the present invention provides valuable manufacturing efficiencies and operational cost-savings.

The barrel adapter 20 may be mounted to the syringe barrel 18 by any appropriate coupling arrangement, as will be understood by those of skill in the art. For example, the barrel adapter 20 may be coupled to the syringe barrel 18 by a coupling structure that may be separate from components of the barrel adapter 20 and syringe barrel 18, or integral with the barrel adapter 20 and the syringe barrel 18. Moreover, the barrel adapter 20 may be coupled to the syringe barrel 18 during the syringe manufacturing process or just prior to use. By way of example only, the syringe adapter 20 may be coupled to the syringe barrel 18 by an interference fit, glue, a snap-fit assembly, and/or a screw-fit assembly, or the like during the syringe manufacturing process. Alternately, for example, the syringe barrel 18 and barrel adapter 20 may include mating threads or a Luer locking arrangement, such that the barrel adapter 20 may be coupled to the syringe barrel 18 just prior to use. In at least one embodiment of the present invention the barrel adapter may be connected to the barrel via a screw-fit assembly with both the barrel adapter and the barrel having corresponding male and female screw pitch portions or components. In another embodiment, one or more coupling structures may be provided to couple the barrel adapter 20 to the barrel 18. One or more O-rings 36 may be provided for disposition between the barrel adapter 20 and the barrel.

The barrel adapter 20 facilitates mounting of a needle 28 (see FIG. 2) to the syringe barrel 18. The barrel adapter 20 includes a barrel tip 32, a needle assembly 42, and a needle retraction mechanism 21. The barrel tip 32 may be coupled to the syringe barrel 18 by any appropriate method, as explained above with regard to the attachment of the barrel adapter 20 to the syringe barrel 18. The barrel tip 32 typically presents a distal end to the safety syringe 10 when coupled to the syringe barrel 18, the needle 28 extending through the distal end of the barrel tip 32 during injection for delivery of an implant. The barrel tip 32 may further include one or more structures that form a part of the needle retraction mechanism 21, as will be explained below.

The needle assembly 42 may generally include a needle 28 and a needle hub 24. O-rings 36 may be provided about the needle hub 24 to facilitate disposal of the needle assembly 42. The needle 28 is configured to pass-through the needle retraction mechanism 21 and the barrel tip 32 such that one end of the needle 28 is within the barrel and the other end the needle 28 passes through an aperture 33 in the barrel tip 32 (see FIG. 3B). A variety of needle retraction mechanisms may be utilized to facilitate needle retraction within the present invention. For example, the needle retraction mechanism may be similar to that disclosed in International Patent Application PCT/US2012/067793 and U.S. patent application Ser. No. 13/693,915, which are incorporated herein in their entirety by reference for all purposes. In at least one embodiment, the needle retraction mechanism 21 includes a biasing member 30 and an actuable locking arrangement 31 that maintains the biasing member 30 in an energized position until such time as the needle 28 of the needle assembly 42 is retracted into the barrel adapter 20. While the locking arrangement 31 may be any appropriate design that maintains the biasing member 30 in an energized position until such time as the needle 28 is to be retracted, in the illustrated embodiment, the locking arrangement 31 includes a locking mechanism 22 and locking aspects 32a that mate to maintain the relative positions of surfaces that maintain the biasing member 30 in an energized position, as will be explained in greater detail below. Upon actuation of the locking arrangement 31, the biasing member 30 causes the needle 28 to retract into the barrel tip 32.

In one such embodiment of a locking arrangement 31, the biasing member 30 is a compression spring. Ends of the spring 30 are disposed adjacent surface 23 of the locking mechanism 22 and surface 35, within the barrel tip 32. The relative positions of the surfaces 23, 35 maintain biasing member 30 in the compressed, energized position prior to injection, or allow the spring 30 to move to a deenergized position to retract the needle 28 following injection. In order to maintain the spring 30 in an energized position, the locking mechanism 22 and the barrel tip 32 include mating structure that may be decoupled to allow the spring 30 to move to a deenergized position. The structure and operation of the needle retraction mechanism 21 will be discussed in greater detail below.

The embodiment shown in FIGS. 1-5 includes a configuration where the locking mechanism 22 is separate from the barrel tip 32. The locking mechanism 22, however, may be configured to be part of, or attached to, the barrel tip 32. As discussed above, the locking mechanism 22 may be a separate component or a dual-purpose component, such as a dual purpose locking mechanism 22 and needle block. In other words, the locking mechanism 22 may contain or activate features that block the needle 28 from translating axially in the distal direction after the retraction mechanism has been activated and the needle 28 has been retracted. Alternatively, a separate needle block 34 component may be utilized as shown in FIGS. 2, 3B and 3C.

FIG. 3B shows a cross-sectioned view of the barrel tip 32 shown in FIG. 3A. In the interests of clarity, however, cross-hatching of the various components has been omitted. As can be seen in FIG. 3B, the biasing member 30 resides at least partially within the barrel tip 32. When in the compressed state, the biasing member 30 resides within the barrel tip 32 at a distal end and within the locking mechanism 22 at a proximal end. The components of the barrel adapter 20 are shown in an exploded view in FIG. 3C. The needle assembly 42, which includes needle hub 24 and needle 28, may be assembled separately from, or together with, the other components of the barrel adapter 20. For example, all of the components may be pre-assembled into a complete barrel adapter 20, as illustrated in FIG. 3A for mating into a barrel, such as barrel 18 illustrated in FIGS. 1 and 2. Alternatively, the components of the needle assembly 42 may be assembled separately from the remaining components of the barrel adapter 20. In this second configuration, the needle assembly 42 may be mounted into the barrel from the proximal end during assembly instead of at the distal end with the barrel adapter 20.

The needle retraction mechanism 21 may be actuated by any appropriate trigger. For example, in the illustrated embodiment, the needle retraction mechanism 21 is actuated by movement of the locking mechanism 22 toward the distal end of the delivery syringe 10. In such a configuration, the needle hub 24 may be forced into contacting and/or depressing on the locking mechanism 22. This contact may disengage the locking mechanism 22 allowing the biasing member 30 to expand in the proximal direction substantially along a longitudinal axis of the barrel 18, thereby causing the locking mechanism 22 and the components of the needle assembly 42, including the needle 28, to retract into the barrel 18. The needle hub 24 may function to retain the needle 28 in a substantially fixed position while the barrel adapter 20, delivery system, and delivery syringe 10 are in a first stage, generally configured for needle injection and implant delivery. Additionally or alternatively, the locking mechanism 22 may function to retain the needle in a substantially fixed position during this first stage for drug injection.

As will be explained in greater detail below, upon disengagement of the locking mechanism 22 and activation of the retraction mechanism, the biasing member or spring 30 is allowed to expand causing the needle assembly 42 to retract in the proximal direction substantially along a longitudinal axis of the barrel. In some embodiments of the present invention, the entire needle assembly 42 is caused to retract, while in other embodiments only certain components thereof, including the needle 28, are caused to retract upon release of the locking mechanism 22 and expansion of the biasing member 30. Similarly, in some embodiments of the present invention the locking mechanism 22 is caused to retract with the needle assembly 42 while in other embodiments the locking mechanism 22 remains substantially stationary, but enables the needle assembly 42, or components thereof, to move.

In some embodiments, following retraction of the needle 28, the barrel adapter 20 may be provided with a block that prevents or inhibits the needle 28 from translating in the distal direction and out of the barrel tip 32. FIG. 3C shows one embodiment of a needle block 34, which may reside within the distal end of the barrel tip 32. The illustrated needle block 34 includes a flange 60 having a central aperture for passage of the needle 28. A pair of arms 62 extends from the flange 60, the distal ends of the arms 62 supporting a pair of clips 64. When the needle block 34 is disposed within the barrel tip 32, the arms 62 bias the clips 64 toward one another. In this embodiment, with the needle 28 extending through the aperture of the flange 60, the clips 64 at the distal end of the needle block 34 expand and permit disposition of the needle 28 between the clips 64 when the needle 28 is in the injection and retraction stages. Upon retraction of the needle 28 in the proximal direction past the clips 64, however, the arms 62 bias the clips 64 to a closed position and do not permit the needle 28 to pass-through in the distal direction. While the assembly may be alternately configured, in this embodiment, a distal end of the biasing member 30 or spring 30 may be disposed adjacent the flange 60 during assembly. It will be appreciated that the needle block 34 illustrated is disclosed by way of example only, and the block may be of an alternate configuration and structure.

According to another aspect of the invention, the delivery syringe 10 and/or the barrel adapter 20 in conjunction with the syringe barrel 18 may be utilized for delivery of an implant 49. As would be appreciated by an ordinarily skilled artisan, the implant 49 may be collectively or individually, depots, implants, beads, pills, capsules, nodules, drug-eluting device, dry or lyophilized drugs or treatments, or other forms of implants or the like, and may include the dispensing of a drug, a powder, a suspension, or the like, or any combination thereof. In order to allow for placement or deployment of an implant 49, the barrel adapter 20 further includes a stylet 54 disposed within the lumen 29 of the needle 28, and, preferably, a multiple stage retraction mechanism.

Figure 6:
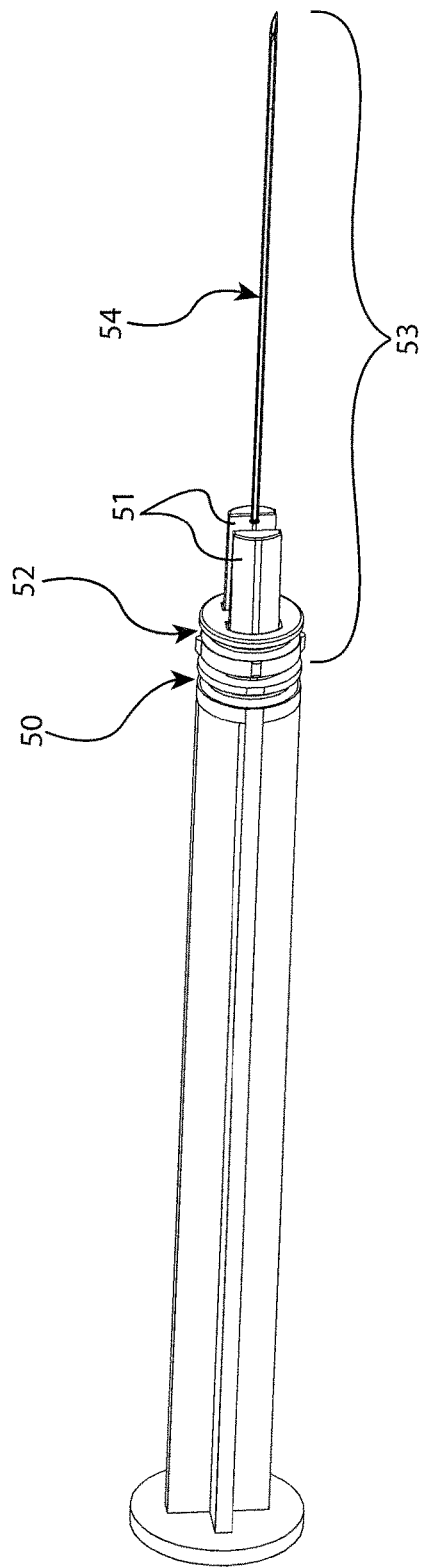
FIG. 6 shows an isometric view of an actuation mechanism including prong base, stylet disc, and stylet, according to an embodiment of the present invention.
Figure 8A:
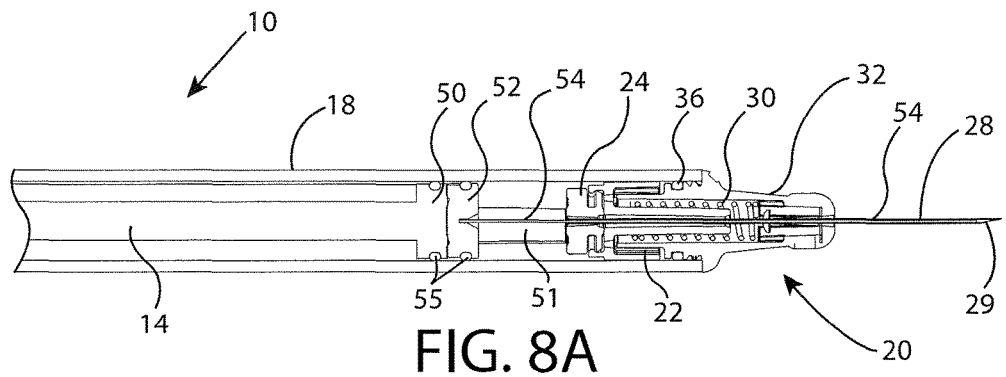
FIGS. 8A-8D show enlarged fragmentary cross-sectional views (cross-hatching being eliminated in the interest of clarity) of the embodiment shown in FIGS. 7A-7D, similarly as the syringe progresses through the stages of needle injection, needle retraction activation, implant delivery, and stylet retraction.
Figure 8B:
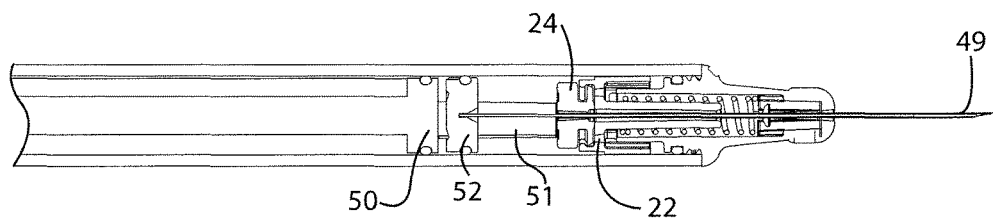
Figure 8C:
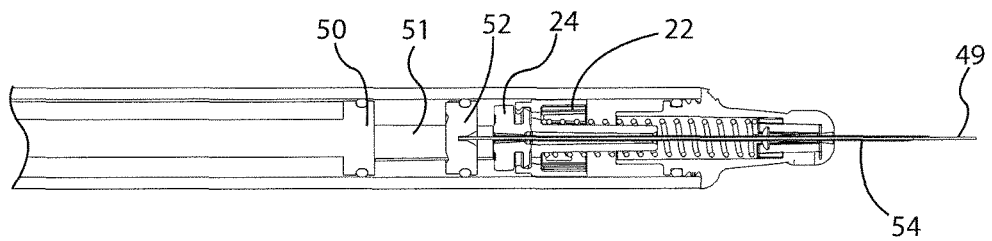
Figure 8D:
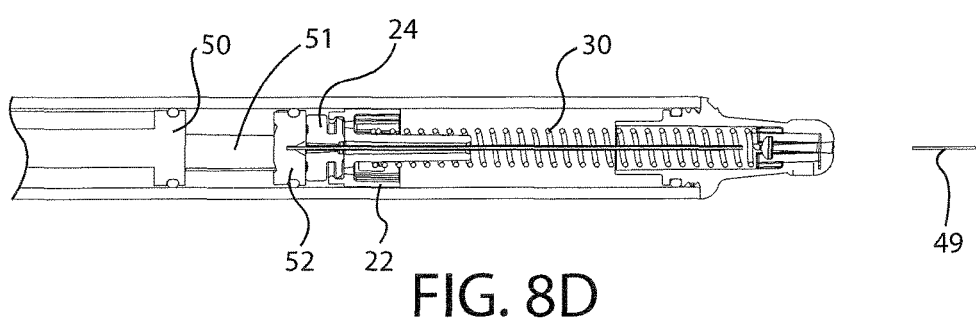

Referring to FIG. 3B, the needle 28 includes a central lumen 29. The needle hub 24 has an aperture 25 that acts as pass-through at its center (e.g., at substantially the longitudinal axis of these components and the barrel). This aperture 25 may have a diameter equal to the outer diameter of the needle 28, such that the needle 28 is retained in position within the needle hub 24 during an initial injection stage and allowed to axially translate in the proximal direction upon activation of the retraction mechanism, with or without the needle hub 24. With the needle 28 disposed within the aperture 25 through the needle hub 24, the proximal end of the needle 28 presents the central lumen 29. Referring to FIGS. 2 and 6, in operation, the stylet 54 is disposed within the central lumen 29 of the needle 28, and an implant 49 to be implanted may be contained in the lumen 29 of needle 28 distally to the stylet 54. Accordingly, when the needle 28 enters the target (not shown), the needle 28 may be retracted axially over the stylet 54. In this way, the stylet 54 prevents the implant 49 from being retracted with the needle 28, leaving the implant 49 in position in the target. Should the stylet 54 extend beyond the barrel tip 32, the stylet 54 may likewise be retracted from the target, either along with the needle 28 following the positioning of the implant 49, or separately from the needle 28 once the needle 28 has been retracted. Thus, according to an aspect of the invention, at least the needle 28 is retracted in order to provide injection of the implant 49. According to another aspect, in some embodiments, the stylet 54 is likewise retracted following delivery of the implant 49.

Figure 5:
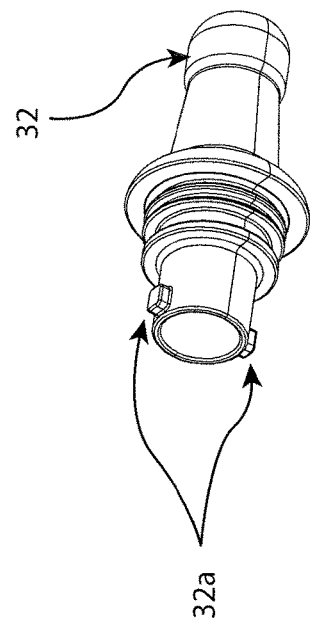
FIG. 5 shows an isometric view of a barrel tip, according to an embodiment of the present invention.

Turning first to the retraction of the needle 28, while any appropriate actuatably locking arrangement 31 may be provided, one embodiment of the actuable locking arrangement 31 is illustrated in FIGS. 3B, 3C, 4, and 5, FIG. 4 showing a locking mechanism 22 and FIG. 5 showing a barrel tip 32. The barrel tip 32 has locking aspects 32a, which are engageable with the locking mechanism 22. In this embodiment, the barrel tip 32 has two locking aspects 32a which engage with receiving structures in the locking mechanism 22. It will be appreciated, however, that the barrel tip 32 may have one or more locking aspects 32a.

Figure 4:
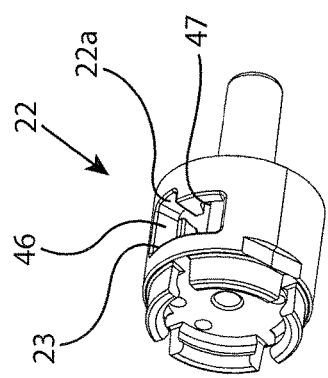
FIG. 4 shows an isometric view of a locking mechanism, according to an embodiment of the present invention.

As shown in FIG. 4, the receiving structures of the locking mechanism 22 may be, for example, in the form of locking portals 46. In the illustrated embodiment, the locking portals 46 are "L" shaped cutouts, although alternate shapes and arrangements are envisioned. One or more channels 47 within the inner diameter of the locking mechanism 22 permit the locking aspects 32a to slide into the locking portals 46 and, upon rotation of the locking mechanism 22, sit at rest within seats 22a of the locking portals 46 of the locking mechanism 22. In this way, the relative positions of locking mechanism 22 and the barrel tip 32 are maintained as the biasing member 30 of this embodiment biases the locking mechanism 22 and the barrel tip 32 apart. While the locking mechanism 22 and the barrel tip 32 of the illustrated embodiment include the locking portals 46 and locking aspects 32a, respectively, it will be appreciated that the locking mechanism 22 and barrel tip 32 could alternately include the locking aspects and the locking portals, respectively, or some other combination, so long as the engagement provides an arrangement that is operable to engageably/releasably couple the associated components. It will further be appreciated that the locking mechanism 22 may be of an alternate structure entirely, so long as the arrangement provides for the retractable disposition of the needle 28 within the syringe, preferably actuable as a result of use of the delivery syringe 10 to inject an implant 49.

In the illustrated embodiment, the needle retraction mechanism 21 is actuated by an axial force applied to the locking mechanism 22. While the axial force may be applied as result of alternate structure, in this embodiment contact by and axial movement of the needle hub 24 causes corresponding movement of the locking mechanism 22 in an axial direction. In actuation, as the locking mechanism 22 is caused to translate in the distal direction, such as by contact by the needle hub 24, the locking mechanism 22 is allowed to disengage from the one or more corresponding locking aspects 32a of the barrel tip 32, allowing the spring 30 to expand and the retraction mechanism to activate. The disengagement of the locking mechanism 22 from the locking aspects 32a may be caused by axial translation of the locking mechanism 22. Additionally or alternatively, the disengagement of the locking mechanism 22 from the locking aspects 32a may be caused by rotation of the locking mechanism 22, such as rotation upon axial translation. The rotation, by itself or in conjunction with the axial translation, enables the locking mechanism 22 to escape from the engagement with the locking aspects 32a. In at least one embodiment, this rotation may be caused by torsionally biasing the compression spring 30, which rotates the locking mechanism 22 in one direction around the axis upon compression. In another embodiment, the rotation may be caused by a configuration of the locking mechanism 22 itself to enable this functionality, such as a pitched aspect profile of the locking mechanism 22, by a shaping of the locking aspects 32a, or by the interface between the locking aspects 32a and locking mechanism 22 which promote this movement and allow for the engagement and disengagement of the components.

The force applied by the user to axially translate the plunger rod 14 may likewise be used to activate the actuable locking arrangement 31 to disengage the locking mechanism 22 from the barrel tip 32 and retract the needle 28. To this end, the plunger rod 14 component of the plunger assembly 12 is disposed to allow for the transmission of a needle retraction actuating force, while the stylet 54 is in a position for injection and implant delivery. In order to allow the transmission of the needle retraction actuating force from the plunger assembly 12 to the needle hub 24 and, ultimately, the locking mechanism 22, at least one actuating prong 51 is disposed to be advanced longitudinally upon movement of the plunger assembly 12 while the stylet 54 remains substantially stationary within the syringe barrel 18.

As may be seen in FIG. 6, in at least one embodiment of the present invention a stylet assembly 53 includes the stylet 54 extending from a support structure in the form of a stylet disc 52 that sits within the syringe barrel 18 to substantially maintain the stylet 54 in position. The stylet disc 52 may be maintained in position within the syringe barrel 18 by way of one or more O-rings. In order to allow for the transmission of force from the plunger assembly 12, there is provided at least one actuating prong 51 dispose to longitudinally traverse through the barrel, and the stylet disc 52 includes at least one passage 53 extending longitudinally through the stylet disc 52 and disposed to receive the at least one actuating prong 51. Although the illustrated embodiment includes two such prongs 51 and passages 53, a greater number may be provided. Further, while the illustrated embodiment provides the at least one passage 53 spaced from a perimeter of the stylet disc 52, it will be appreciated by those of skill in the art that the at least one passage 53 could alternatively or additionally be disposed along the perimeter of the stylet disc 52, such that the interior wall of the syringe barrel 18 may likewise form a portion of the longitudinally extending passage 53. It will be further understood that the number of passages 53 and prongs 51 need not be identical. For example, a single passage 53 may allow for the passage 53 of more than one prong 51.

The prongs 51 extend from a base 50, which is disposed to be moveable in an axial direction within the syringe barrel 18. The prong base 50 may be maintained in position within the syringe barrel 18 by way of one or more O-rings. While the base 50 is illustrated as having a disc shape, it will be appreciated that it may have an alternate shape so long as the base 50 maintains supports the prongs 51 and facilitates their movement within the barrel 18. In operation, axial movement of the plunger assembly 12 causes the movement of the base 50 and associated prongs 51 so that the prongs 51 contact the needle hub 24. Thus, in the illustrated embodiment, the prongs 51 may be made to contact the needle hub 24 such that force applied to the plunger rod 14 by a user is applied to the base 50 and transferred, at least in part, to the needle hub 24. Through this transfer, a surface of the needle hub 24, or similar aspect thereof, may be caused to push upon or otherwise initiate the release of the locking mechanism 22 from the engaged connection with the locking aspects 32a of the barrel tip 32. By releasing the locking mechanism 22 from the locking aspects 32a of the barrel tip 32, the biasing member 30 (e.g., spring) is allowed to expand and retract the needle assembly 42 including the needle 28 in the proximal direction substantially along a longitudinal axis of the barrel 18. In such embodiments of the present invention, the needle 28, needle hub 24, and locking mechanism 22 are caused to retract upon release of the locking mechanism 22 and expansion of the biasing member 30.

It will be appreciated that the prongs 51, base 50 and plunger assembly 12 may be separately fabricated, or one or more aspects of the same may be formed as a unit, formed separately and later assembled, or remain as separate units that engage one another during assembly or use of the delivery syringe 10. In the embodiment illustrated in FIG. 6, the prongs 51, base 50 and plunger rod 14 are unitarily formed, the prongs 51, base 50, and plunger rod 14 moving axially as a single unit as the plunger assembly 12 is depressed. In an alternate embodiment, for example, the base 50 and prongs 51 may be formed unitarily, such that the plunger rod 14 engages the base 50 to move the base 50 and associated prongs 51 as the plunger rod 14 is pushed forward in the syringe barrel 18.

In assembly, the stylet 54, which is substantially coaxial to the needle 28, is placed in the lumen 29 of the needle 28. In an embodiment, the stylet 54 may be partially overlapping the needle 28 from the non-patient end (i.e., the proximal end P). The implant 49 is placed in the lumen 29 of the needle 28 between the stylet 54 and the patient end of the needle 28 (i.e., the distal end D).

In use, an actuation mechanism, such as a plunger rod 14, may be utilized to activate a needle retraction mechanism 21, causing the needle 28 to retract. Initially, the stylet 54 is stationary relative to the needle 28; retraction of the needle 28 by the needle retraction mechanism 21 exposes the implant 49 in the target area for delivery. The stylet 54 ensures that the implant 49 does not follow the needle 28 as it retracts.

According to an aspect of the invention, in order to ensure accurate delivery of the implant 49, the stylet 54 retracts only after the distal end of the stylet 54 is past the distal end of the retracting needle 28. In the illustrated embodiment, the sequence and timing of retraction of the stylet 54 is such that a mechanism for the retraction of the stylet 54 is activated or triggered after the retraction of the distal end of the needle 28 past the distal end of the stylet 54, although the same retraction mechanism may be used to retract both components. A stylet disc 52 that is proximal to the needle retraction mechanism 21 may be utilized to ensure the desired sequence of retraction. The distance between the needle retraction mechanism 21 and the stylet disc 52 sets the sequence and/or timing of retraction of the stylet 54 relative to the needle 28. In the illustrated embodiment, the stylet retraction mechanism is the engagement of the needle hub 24 with the stylet disc 52.

FIGS. 7A-7D show a delivery syringe 10 including a barrel adapter 20, a retraction mechanism 21, and a delivery system according to one embodiment of the present invention, as the syringe 10 progresses through the stages of: needle injection, needle retraction activation, implant delivery, and stylet retraction. FIG. 7A shows the barrel adapter 20 mounted with the barrel 18. In packaging, the barrel adapter 20 may contain a rigid needle shield (RNS) which removably engages with barrel tip 32 to protect the user from the needle 28. FIG. 7A shows the syringe with the RNS removed and the needle 28 exposed for injection into a patient. The lumen 29 of the needle 28, between the stylet 54 and the needle tip, contains a drug implant 49 for injection. FIG. 7B shows the syringe after the retraction mechanism 21 has been activated, with the plunger rod 14 depressed axially in the distal direction, and the prong base 50 in contact with the needle hub 24. Upon minimal further depression of the plunger rod 14, the retraction mechanism 21 is activated and the locking mechanism 22 is permitted to rotate axially by, for example, torsional bias of the biasing member 30. Upon axial rotation of the locking mechanism 22, the locking mechanism 22 is permitted to disengage from the locking aspects 32a of the barrel tip 32 as described above.

As shown in FIG. 7C, the biasing member 30 is permitted to expand axially in the proximal direction. The proximal end of the biasing member 30 pushes upon the locking mechanism 22 in the proximal direction, which pushes upon the needle hub 24 and the needle 28 causing the needle 28 to retract into the barrel 18. This action, coupled with the non-movement of the stylet 54 with the needle 28, exposes the implant 49 for targeted delivery to the patient. After the implant 49 is fully exposed and delivered, the stylet 54 is caused to retract with the needle 28. This action is caused by the stylet disc 52 coming into contact with the needle hub 24, and both components retracting together. As mentioned above, these dimensions are controlled to ensure that retraction of the stylet 54 occurs only after the implant 49 has been delivered. FIG. 7D shows the syringe after retraction of the needle 28 and stylet 54 has completed. FIGS. 8A-8D show enlarged cross-sectional views of the embodiment shown in FIGS. 7A-7D, showing the relationship of the components as the syringe progresses through the stages of: needle injection, needle retraction activation, implant delivery, and stylet retraction.

In another embodiment, the present invention provides a delivery syringe having a barrel adapter capable of mounting to the barrel via a screw-fit connection. Such a configuration may facilitate an automated implant insertion process for loading the implant into the needle of the barrel adapter, as will be described further herein. FIG. 9A shows a side elevational view of a delivery syringe 100 including a barrel adapter 120 with a screw-fit connection, according to one such embodiment of the present invention. Such delivery syringes may utilize a needle cap 170, shown as a transparent component in FIG. 9B for clarity, to facilitate attachment of the barrel adapter 120 containing the implant to the barrel 118 of the delivery syringe 100. The barrel adapter 120 may reside fully within the needle cap 170 in, for example, a sterile environment closed by a removable membrane 171, for packaging, transport, and/or assembly. The barrel adapter 120 may be shipped, for example, to a filler or a pharmaceutical company within a sterile needle cap 170 for insertion of the implant and final assembly with the barrel 118 of the delivery syringe 100. In at least one embodiment the distal tip of the needle 128 of the barrel adapter 120 is plugged, such as by a biodegradable polymer, by the manufacturer prior to shipping the sterile needle cap 170 containing the barrel adapter 120 to the filler or pharmaceutical company. Upon receiving the needle cap 170 separate from the barrel 118 and other components of the delivery syringe 100, the filler or pharmaceutical company may peel away or otherwise remove the removable membrane 171 and insert the implant through the proximal end of the barrel adapter 120. The barrel adapter 120 may then be attached or mounted to the barrel 118 of the delivery syringe 100 with or without the assistance of the needle cap 170. The delivery syringe is configured such that assembly of the barrel adapter 120 to the barrel 118 is possible only when the stylet 154 is axially aligned with and inserted into the proximal end of the needle 128 through an aperture of the needle hub 124. The configuration, dimensions, and design of the barrel adapter, barrel tip, and/or other components of the delivery syringe may assist in the assembly and operation of the device. For example, in at least one embodiment of the present invention, the barrel adapter and/or barrel tip may have a substantially conical shape or conical portion. This may correlate to a conical inner cross-section of such components as well. The conical shape or portion may be utilized to, for example, permit accurate alignment of the components (such as the coaxial alignment of the stylet and the needle cannula), ensure placement of the implant within the lumen of the needle cannula during assembly and filling of the implant, and/or ensure proper alignment, relative motion, or other operation parameters of the components during the use of the delivery syringe. FIG. 9C shows a side elevational view of the delivery syringe and barrel adapter shown in FIG. 9A in such an assembled configuration.

Notably, these embodiments of the present invention show a configuration wherein the one or more prongs 151 are detached or separate components from prong base 150. In such embodiments, the one or more prongs perform the same relative functions as the prongs utilized in the delivery syringe described above with reference to FIG. 1. However, in the embodiment shown in FIG. 9C the prongs extend, in the proximal direction, from a stylet guide 155 rather than extending, in the distal direction, from a prong base, as shown in FIG. 1. Regardless of the configuration, the prongs 151 are configured to permit the stylet disc 152 to translate axially upon the prongs 151 to control the position of the stylet 154 as the delivery syringe progresses through the stages of operation. In either the embodiment shown in FIG. 1 or the embodiment shown in FIG. 9C, the prongs 151 may also be utilized to activate the needle retraction mechanism by conveying the force applied to the plunger rod 114 by the user to the locking mechanism 122. FIGS. 10B and 10C show enlarged views of the stylet disc 152 and stylet 154, which interact with the stylet guide 155 and prongs 151 during operation of the delivery syringe 100.

As described above, the embodiments of the present invention may simplify the assembly, manufacturing, and operation of the implant delivery syringe. These processes may be facilitated by the use of an optional plunger guide assembly 112, as shown in FIG. 10A. In one embodiment, the plunger guide assembly 112 includes barrel cap 116 and a plunger rod 114 having a base 150. The barrel cap 116 may have a port 116A within which a guide pin 117 may be positioned. The guide pin 117 may interact with the plunger rod 114, such as with channels, pass-throughs, and stop members of the plunger rod 114, for example, to guide the assembly, manufacturing, and operation of the delivery device. FIGS. 11A-11C show side elevational views of a plunger rod 114, according to at least one embodiment of the present invention, rotated relative to guide pin 117 around axis A at 90 degree intervals, respectively, as indicated by arrow R. FIG. 11A shows a plunger rod 114 having a stop member 114D, a pass-through 114A, a channel 114E, and a base connection aspect 114C. The base connection aspect 114C may be utilized to connect the plunger rod 114 to a base 150, as shown in FIG. 12. In such a configuration, a pin guide 117 may reside within channel 114E and permit axial translation of the plunger rod 114 until the pin guide 117 contacts stop member 114D.

The configuration shown in FIG. 11A may be used, for example, for initial assembly and shipping from the manufacturer to the filler or pharmaceutical company. In this configuration, stop member 114D prevents axial translation in the distal direction of the plunger rod. Optionally, the barrel cap 116 may interact with the plunger rod 114 and be utilized to prevent axial translation in the proximal direction of the plunger rod. FIG. 11B shows the plunger rod 114 having been rotated 90 degrees in the direction indicated by arrow R about axis A such that the guide pin 117 is permitted to move between channel 114E through pass-through 114A to channel 114F. In this configuration, the filler or pharmaceutical company may translate the plunger rod 114 to position the stylet disc 152 and stylet 154 for final assembly and operation. The transition from the configuration shown in FIG. 11A to the configuration shown in FIG. 11B may, for example, permit placement of the implant into the barrel adapter prior to attachment of the barrel adapter to the barrel of the delivery syringe, as described above. The delivery syringe may be shipped to the user in the configuration shown in FIG. 11B. Prior to use, the user may rotate the plunger rod 114 another 90 degrees in the direction indicated by arrow R about axis A. This rotation may permit the guide pin 117 to move between channel 114F, through pass-through 114B, to channel 114G (as shown in FIG. 11C). In the configuration shown in FIG. 11C, the plunger rod 114 is permitted to freely translate axially in the distal and proximal directions to facilitate deployment of the implant and retraction of the needle and stylet. FIG. 12 shows an enlarged cross-sectional view (cross-hatching being eliminated in the interest of clarity) of delivery syringe 100 with the interaction between the guide pin 117 and plunger rod 114 visible through the barrel cap 116.

FIGS. 13A-13D show enlarged cross-sectional views (cross-hatching being eliminated in the interest of clarity) as the delivery syringe 100 progresses through the stages of needle injection, needle retraction activation, implant delivery, and stylet retraction. As may be seen in FIG. 13A, in at least one embodiment of the present invention a stylet assembly includes the stylet 154 extending from a support structure in the form of a stylet disc 152 that sits within the syringe barrel 118 to substantially maintain the stylet 154 in an initial position. The stylet disc 152 may be maintained in position within the syringe barrel 118 by way of one or more O-rings. Notably, the stylet disc 152 and stylet 154 are held substantially in a fixed position by the O-rings or by equivalent means during the initial stages of operation to maintain the implant 129 in a fixed position until the needle 128 is retracted proximally to expose the implant for deployment. This initial position of the stylet assembly is maintained until the stylet disc 152 is contacted by the stylet guide 154 upon retraction of the needle hub 124 and needle 128. As shown in FIGS. 13A-13D, the needle 128 is retracted upon activation of the needle retraction mechanism to expose the implant 129 for deployment by the stylet 154, followed by retraction of the stylet 154 into the barrel 118. When a plug 127 is utilized to initially retain the implant 129 in position at the distal tip of the needle 128, the plug 127 may optionally be deployed in addition to deployment of the implant 129.

Figure 13A:
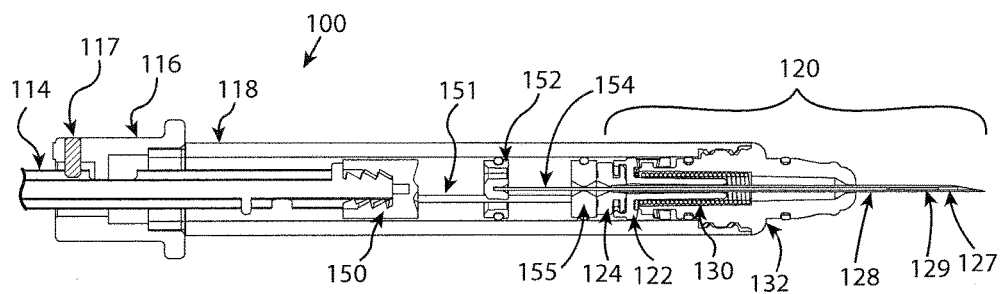
FIGS. 13A-13D show enlarged fragmentary cross-sectional views (cross-hatching being eliminated in the interest of clarity) of the embodiment shown in FIG. 9A, as the syringe progresses through the stages of needle injection, needle retraction activation, implant delivery, and stylet retraction.

As shown in FIG. 13A, the stylet guide 155 may be caused to contact the needle hub 124 by force applied upon the prongs 151 by the plunger rod 114 and/or base 150. In the illustrated embodiment, the stylet guide 155 may be made to contact the needle hub 24 such that force applied to the plunger rod 114 by a user is applied to the base 150 and transferred, at least in part, to the needle hub 124. Through this transfer, a surface of the needle hub 124, or similar aspect thereof, may be caused to push upon or otherwise initiate the release of the locking mechanism 122 from the engaged connection with the locking aspects of the barrel tip 132. By releasing the locking mechanism 122 from the locking aspects of the barrel tip 132, the biasing member 130 (e.g., spring) is allowed to expand and retract the needle assembly including the needle 128 in the proximal direction substantially along a longitudinal axis of the barrel 118. In such embodiments of the present invention, the needle 128, needle hub 124, and locking mechanism 122 are caused to retract upon release of the locking mechanism 122 and expansion of the biasing member 130. Initially, the stylet 154 is stationary relative to the needle 128; retraction of the needle 128 by the needle retraction mechanism exposes the implant 129 in the target area for delivery. The stylet 154 ensures that the implant 129 does not follow the needle 128 as it retracts. In order to ensure accurate delivery of the implant 129, the stylet 154 retracts only after the distal end of the stylet 154 is past the distal end of the retracting needle 128. In the illustrated embodiment, the sequence and timing of retraction of the stylet 154 is such that a mechanism for the retraction of the stylet 154 is activated or triggered after the retraction of the distal end of the needle 128 past the distal end of the stylet 154, although the same retraction mechanism may be used to retract both components. Similar to the embodiment described above with reference to FIG. 1, stylet disc 152 is proximal to the needle retraction mechanism and may be utilized to ensure the desired sequence of retraction. The distance between the needle retraction mechanism and the stylet disc 152 may be utilized to set the sequence and/or timing of retraction of the stylet 154 relative to the needle 128.

Figure 13B:
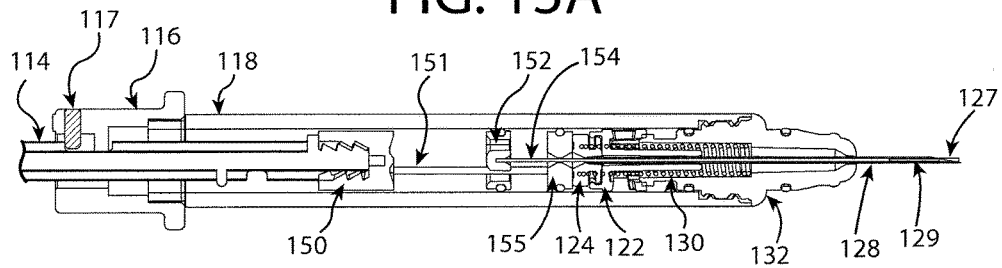
Figure 13C:
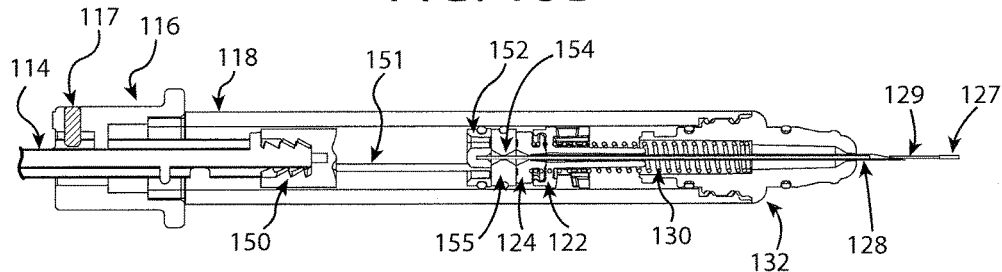
Figure 13D:
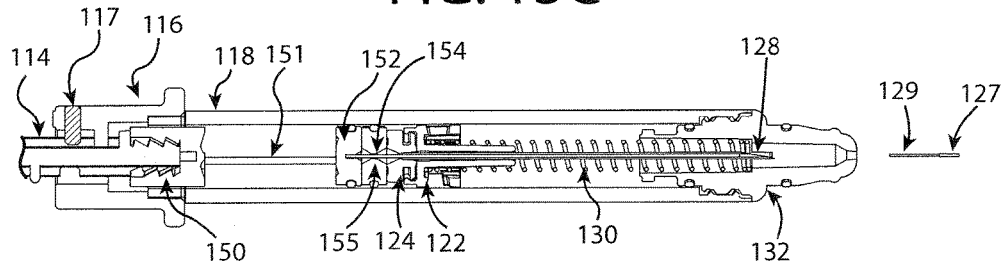

Upon activation of the needle retraction mechanism the needle 128 is retracted into the barrel 118 of the delivery syringe 100, thereby exposing the implant 129 for deployment to the target location. Retraction of the needle assembly, including needle hub 124 and needle 128, causes needle hub 124 to contact and retract the stylet guide 155. As shown in FIG. 13B, the stylet disc 152 and stylet 154 are retained in substantially a constant position to retain the implant 129 in a relatively fixed position as the needle 128 retracts around it. As the implant 129 is exposed from the needle 128 for deployment, as shown in FIG. 13C, the stylet guide 155 contacts and retracts the stylet disc 152 and, thereby, the stylet 154. Notably, because the retraction of the needle assembly and the stylet guide 155 results in the axial translation of the prongs 151 in the proximal direction, the plunger rod 114 and/or base 150 are also caused to axially translate in the proximal direction. This permits the user, by maintaining contact with the plunger rod 114, to control the retraction of the needle assembly and deployment of the implant. As shown in FIG. 13D, at the end of implant deployment the needle 128 and stylet 154 are fully retracted and safely contained within the barrel 118 of the delivery syringe 100. As described above, optional guide pin 117 may be utilized with plunger rod 114 to control the functions of the delivery syringe 100. Accordingly, embodiments of the present invention allow for accurate delivery of the drug implants to target locations while remaining easy-to-use and preventing needle-stick injuries.

Embodiments of the present invention also provide configurations which allow the use of standard, commercially-available components, thereby reducing overall manufacturing costs, streamlining assembly processes, and avoiding regulatory concerns often associated with non-standard materials and components. For example, the barrel may be made of certain plastics, glass, or any other material commonly used for medical grade products. One or more components of the present invention may also be made up of certain plastics, such as the polycarbonate plastics sold under the trade name "LEXAN" by SABIC Innovative Plastics of Pittsfield, Mass. Similarly, certain elastomeric polymers or rubbers may be utilized, such as the rubber products sold under the trade name "HELVOET" by Datwyler Pharma Packaging USA Inc. of Pennsauken, N.J., for components such as a needle seal, if provided, and the prong base 50. Various medical grade metals, such as stainless steel, may be utilized for the needle, as would be appreciated by an ordinarily skilled artisan. These components, the barrel adapters, and the delivery syringes may be shaped or sized in a myriad of different configurations to meet the desired parameters. These components, barrel adapters, and syringes may be assembled, and/or filled with an implant, by a multitude of processes known in the art. For example, well known glues or welding methods such as ultrasonic welding may be employed to assemble the components of the present invention.

The delivery syringes of the present invention are configured to be used in a manner similar to conventional syringes. The method of use includes the steps: depressing the plunger assembly 12 to facilitate activation of the retraction mechanism 21 and delivery of the implant 49 from the needle 28; triggering the locking mechanism 22 to release the biasing member 30 from its energized state by contact between the biasing member 30 and the needle assembly 42, causing the needle assembly 42 to retract into the barrel; delivering the implant 49 to the target location; and, upon delivery of the implant 49, retracting the stylet 54 into the barrel of the syringe. As discussed above with regard to embodiments of the syringes, there are a number of different ways that the locking mechanism 22, needle hub 24, and other components may be configured to function to enable the engagement and release of the biasing member 30. For example, in syringe 10, the locking mechanism 22 may include an interface on the barrel tip 32 which engages the locking mechanism 22. Upon activation by the user, the needle hub 24 may be employed to initiate the release of the locking mechanism 22 from its engagement with the barrel tip 32. In another embodiment of the syringe, the locking aspects 32*a* may be separate components from barrel tip 32, but function in a manner similar to the components of syringe 10. The functionality of delivery syringe 100 is substantially similar to that described herein with regard to delivery syringe 10.

Regardless of the particular components, the methods of use for the delivery syringes of the present invention are relatively similar. By releasing the locking mechanism 22 from its engaged condition, the biasing member 30 is allowed to expand causing the needle assembly 42 to retract in the proximal direction substantially along a longitudinal axis of the barrel 18. In some embodiments of the present invention, the entire needle assembly 42 is caused to retract, while in other embodiments only certain components thereof, including the needle 28, are caused to retract upon release of the locking mechanism 22 and activation of the biasing member 30. Similarly, in some embodiments of the present invention the locking mechanism 22 is caused to retract with the needle assembly 42, while in other embodiments the locking mechanism 22 remains substantially stationary, but enables the needle assembly 42, or components thereof, to move. Optionally, the method of use may include the step of blocking, with a needle block, the needle 28 from axially translating in the distal direction after the needle assembly 42 has retracted into the barrel 18.

The present invention provides component assemblies, such as barrel adapters, delivery systems, retraction mechanisms which provide needle retraction, delivery syringes which integrate such safety mechanisms, methods of manufacturing such delivery syringes, and their methods of use. As stated above, the barrel adapters, delivery systems, retraction mechanisms, and delivery syringes may be utilized in a number of different configurations. For example, as stated above, the novel barrel adapters of the present invention are configured to mate with, be mounted in, or otherwise connect to a barrel, however it may be desirable to pre-form any of the components of the barrel adapter to the barrel. Such modifications are contemplated by and encompassed in embodiments of the present invention. Components may be single components, unified components, or multi-purpose components, as described in embodiments discussed above. Furthermore, there are a number of different configurations which may utilize the novel needle retraction mechanisms described herein, which may leverage the interaction of the needle 28, stylet 54, needle hub 24, stylet disc 52, and prong base 50, and related components. Accordingly, similar to the examples provided above, the barrel adapters and delivery syringes of the present invention may be configured, modified, and utilized to initiate drug implant delivery and activate needle retraction in any number of configurations, while remaining within the breadth and scope of the present invention. Thus, it is intended that the present invention covers the modifications and variations of this invention provided they come within the scope of the appended claims and their equivalents.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A barrel adapter for a delivery syringe having a barrel and a plunger assembly adapted to move within the barrel, the adapter comprising:
   a barrel tip adapted to be sealingly engaged with a distal end of the barrel,
   a needle assembly including a needle and a needle hub through which the needle extends, the needle having a lumen, the needle assembly being disposed at least partially within the barrel tip, the needle adapted to move from an injection position in which the needle extends from a distal end of the barrel tip to a retracted position,
   a stylet assembly including a stylet and a stylet disc, the stylet being axially slidable and at least partially disposed within the needle lumen, the stylet being proximally disposed and spaced from a distal tip of the needle when the needle is in the injection position,
   a drug implant within the lumen of the needle;
   a plug within the lumen of the needle located distally of the drug implant, and
   a needle retraction mechanism, the needle retraction mechanism including a biasing member and an actuable locking arrangement, the locking arrangement being disposed to maintain the biasing member in an energized position when the locking arrangement is locked and to release the biasing member when actuated, the biasing member being disposed to provide relative motion of the needle and stylet from the injection position to the retracted position when the biasing member is released from the energized position, the barrel tip configured to sealingly engage an inner perimeter of the barrel to mount the needle assembly, the stylet assembly, and the needle retraction mechanism within the barrel through a distal end of the barrel.

2. The barrel adapter of claim 1, wherein the plug is a biodegradable polymer plug from the group consisting of water-soluble polymers, PLGA, CAHP, and combinations thereof.

3. The barrel adapter of claim 1 further comprising a stylet retraction mechanism.

4. An automatically retractable implant delivery syringe comprising;
   a barrel having a distal end and a proximal end,
   a plunger assembly adapted to move within the barrel,
   a barrel tip sealingly engaged with a distal end of the barrel,
   a needle assembly including a needle and a needle hub through which the needle extends, the needle having a lumen, the needle assembly being disposed at least partially within the barrel tip, the needle adapted to move from an injection position in which the needle extends from a distal end of the barrel tip to a retracted position,
   a stylet assembly including a stylet and a stylet disc, the stylet being axially slidable and at least partially disposed within the needle lumen and is proximally disposed spaced from a distal tip of the needle when the needle is in the injection position,
   a drug implant within the lumen of the needle;
   a plug within the lumen of the needle located distally of the drug implant, and
   a needle retraction mechanism, the needle retraction mechanism including a biasing member and an actuable locking arrangement, the locking arrangement being disposed to maintain the biasing member in an energized position when the locking arrangement is locked and to release the biasing member when actuated, the biasing member being disposed to provide relative motion of the needle and stylet from the injection position to the retracted position when the biasing member is released from the energized position, the barrel tip configured to sealingly engage an inner perimeter of the barrel to mount the needle assembly, the stylet assembly, and the needle retraction mechanism within the barrel through a distal end of the barrel.

5. The syringe of claim 4 wherein the plug is a biodegradeable polymer plug from the group consisting of water-soluble polymers, PLGA, CARP, and combinations thereof.

* * * * *

UNITED STATES PATENT AND TRADEMARK OFFICE
CERTIFICATE OF CORRECTION

PATENT NO. : 10,342,966 B2
APPLICATION NO. : 14/708778
DATED : July 9, 2019
INVENTOR(S) : Gautam N. Shetty et al.

It is certified that error appears in the above-identified patent and that said Letters Patent is hereby corrected as shown below:

In the Claims

In Claim 5, Column 30, Line 62, please delete "CARP" and insert --CAHP--.

Signed and Sealed this
Twenty-seventh Day of August, 2019

Andrei Iancu
*Director of the United States Patent and Trademark Office*